United States Patent
Persson

(10) Patent No.: US 7,235,638 B2
(45) Date of Patent: Jun. 26, 2007

(54) COAGULATION FACTOR VII DERIVATIVES

(75) Inventor: Egon Persson, ÅAkarp (SE)

(73) Assignee: Novo Nordisk HealthCare A/G, Zurich (CH)

( * ) Notice: Subject to any disclaimer, the term of this patent is extended or adjusted under 35 U.S.C. 154(b) by 0 days.

(21) Appl. No.: 10/109,498

(22) Filed: Mar. 22, 2002

(65) Prior Publication Data

US 2003/0044908 A1 Mar. 6, 2003

Related U.S. Application Data

(60) Provisional application No. 60/281,261, filed on Apr. 3, 2001.

(30) Foreign Application Priority Data

Mar. 22, 2001 (DK) ............................... 2001 00477

(51) Int. Cl.
  A61K 35/14 (2006.01)
  A61K 38/48 (2006.01)
  A61K 38/00 (2006.01)
  C12N 9/48 (2006.01)
  C12N 9/64 (2006.01)
  A01N 37/18 (2006.01)

(52) U.S. Cl. ...................... 530/381; 435/212; 435/226; 424/94.63; 514/2; 514/12

(58) Field of Classification Search ................ 530/384; 435/212, 226; 424/94.63
  See application file for complete search history.

(56) References Cited

U.S. PATENT DOCUMENTS 4,179,337 A   12/1979  Davis et al. ................. 435/181
5,166,322 A   11/1992  Shaw et al. .................. 530/351
5,206,344 A    4/1993  Katre et al. .................. 530/351
5,861,374 A *  1/1999  Berkner et al. ................. 514/8
2003/0096338 A1* 5/2003 Pedersen et al. ........... 435/69.1
2003/0100075 A1* 5/2003 Persson et al. ............ 435/69.6
2003/0170863 A1* 9/2003 Persson et al. ............. 435/226

FOREIGN PATENT DOCUMENTS

| EP | 0200421 B1 | 7/1993 |
| WO | WO 92/15686 | 9/1992 |
| WO | WO 94/27631 | 12/1994 |
| WO | WO 96/12800 | 5/1996 |
| WO | WO 97/47651 | 12/1997 |
| WO | WO 98/32466 | 7/1998 |
| WO | WO 99/13063 | 3/1999 |
| WO | WO 01/58935 A2 | 8/2001 |
| WO | WO 01/83725 A1 | 11/2001 |

OTHER PUBLICATIONS

Takeya et al. Bovine Factor VII (Oct. 18, 1988), Journal of Biological Chemistry vol. 263 (29) pp. 14868-14877.*
Dickinson et al., Proc. Natl. Acad. Sci. USA, vol. 93, pp. 14379-14384 (1996).
Nucci et al., Advanced Drug Delivery Reviews, vol. 6, pp. 133-151 (1991).
Goodson et al., Bio/Technology, vol. 8, pp. 343-346 (1990).

\* cited by examiner

Primary Examiner—Scott D. Priebe
Assistant Examiner—Maria Marvich
(74) Attorney, Agent, or Firm—Reza Green

(57) ABSTRACT

The present invention relates to novel human coagulation Factor VII polypeptides, Factor VII derivatives as well as polynucleotide constructs encoding such polypeptides, vectors and host cells comprising and expressing the polynucleotide, pharmaceutical compositions, uses and methods of treatment.

9 Claims, 2 Drawing Sheets

COAGULATION FACTOR VII DERIVATIVES

CROSS REFERENCE TO RELATED APPLICATIONS

This application claims priority under 35 U.S.C. 119 of Danish application no. PA 2001 00477 filed on Mar. 22, 2001, and U.S. provisional application No. 60/281,261 filed on Apr. 3, 2001, the contents of which are fully incorporated herein by reference.

FIELD OF THE INVENTION

The present invention relates to novel human coagulation Factor VII derivatives, Factor VII polypeptides, as well as polynucleotide constructs encoding such polypeptides, vectors and host cells comprising and expressing the polynucleotide, pharmaceutical compositions comprising Factor VII derivatives, uses and methods of treatment.

BACKGROUND OF THE INVENTION

Blood coagulation is a process consisting of a complex interaction of various blood components (or factors) that eventually gives raise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa).

Initiation of the haemostatic process is mediated by the formation of a complex between tissue factor, exposed as a result of injury to the vessel wall, and Factor VIIa. This complex then converts Factors IX and X to their active forms. Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. This process includes generation of Factor Xa by Factor IXa (in complex with factor VIIIa) and occurs on the surface of activated platelets. Thrombin finally converts fibrinogen to fibrin resulting in formation of a fibrin clot.

Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa, Factor VIIa or thrombin in vitro. Factor Xa is believed to be the major physiological activator of Factor VII. The conversion of zymogen Factor VII into the activated two-chain molecule occurs by cleavage of an internal $Arg_{152}$-$Ile_{153}$ peptide bond.

It is often desirable to stimulate or to selectively block the coagulation cascade in a subject. Factor VIIa has been used to control bleeding disorders that have several causes such as clotting factor deficiencies (e.g. haemophilia A and B or deficiency of coagulation Factors XI or VII) or clotting factor inhibitors. Factor VIIa has also been used to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Wille-brand's disease. Bleeding is also a major problem in connection with surgery and other forms of tissue damage.

European Patent No. 200,421 (ZymoGenetics) relates to the nucleotide sequence encoding human Factor VII and the recombinant expression of Factor VII in mammalian cells.

Dickinson et al. (*Proc. Natl. Acad. Sci. USA* 93, 14379–14384, 1996) relates to Factor VII polypeptides wherein Lys 157, Val158, Glu296, Met298, Asp334, Ser336 or Lys337 have been individually replaced by Ala. Iwanaga et al. (*Thromb. Haemost.* (supplement august 1999), 466, abstract 1474) relates to Factor VIIa variants wherein residues 316–320 are deleted or residues 311–322 are replaced with the corresponding residues from trypsin.

Anticoagulants such as heparin, coumarin, derivatives of coumarin, indandione derivatives, or other agents may be used to selectively block the coagulation cascade in a patient, for example, during kidney dialysis, or to treat deep vein thrombosis, disseminated intravascular coagulation (DIC), and a host of other medical disorders. For example, heparin treatment or extracorporeal treatment with citrate ion (U.S. Pat. No. 4,500,309) may be used in dialysis to prevent coagulation during the course of treatment. Heparin is also used in preventing deep vein thrombosis in patients undergoing surgery.

Treatment with heparin and other anticoagulants may, however, have undesirable side effects. Available anticoagulants generally act throughout the body, rather than acting specifically at a clot site. Heparin, for example, may cause heavy bleeding. Furthermore, with a half-life of approximately 80 minutes, heparin is rapidly cleared from the blood, necessitating frequent administration. Because heparin acts as a cofactor for antithrombin II (AT III), and AT III is rapidly depleted in DIC treatment, it is often difficult to maintain the proper heparin dosage, necessitating continuous monitoring of AT III and heparin levels. Heparin is also ineffective if AT III depletion is extreme. Further, prolonged use of heparin may also increase platelet aggregation and reduce platelet count, and has been implicated in the development of osteoporosis. Indandione derivatives may also have toxic side effects.

In addition to the anticoagulants briefly described above, several naturally occurring proteins have been found to have anticoagulant activity. For example, Reutelingsperger (U.S. Pat. No. 4,736,018) isolated anticoagulant proteins from bovine aorta and human umbilical vein arteries. Maki et al. (U.S. Pat. No. 4,732,891) disclose human placenta-derived anticoagulant proteins. In addition, AT III has been proposed as a therapeutic anticoagulant (Schipper et al., *Lancet* 1 (8069): 854–856 (1978); Jordan, U.S. Pat. No. 4,386,025; Bock et al., U.S. Pat. No. 4,517,294).

In about 30% or more of patients treated by angioplasty, endarterectomy or bypass grafts, thrombosis and/or smooth muscle cell proliferation in the intima causes re-occlusion of the vessel and consequent failure of the reconstructive surgery. This closure of the vessel subsequent to surgery is known as restenosis. Restenosis is thought to result from a complex interaction of biological processes including platelet deposition and thrombus formation, release of chemotactic and mitogenic factors, and the migration and proliferation of vascular smooth muscle cells into the intima of the dilated arterial segment.

The inhibition of platelet accumulation at sites of mechanical injury can limit the rate of restenosis in human subjects. While platelet accumulation occurs at sites of acute vascular injuries, the generation of thrombin at these sites may be responsible for the activation of the platelets and their subsequent accumulation.

International Application No. WO 92/15686 relates to inactivated Factor VIIa, polynucleic acid and mammalian cell lines for the production of inactivated Factor VIIa, and compositions comprising inactivated Factor VIIa for inhibiting blood coagulation.

International Application No. WO 94/27631 relates to methods for inhibiting vascular restenosis, tissue factor activity, and platelet deposition.

International Application No. WO 96/12800 relates to a method for treatment of acute closure of a coronary artery comprising to the individual a composition which comprises inactivated Factor VIIa in conjunction with tissue plasminogen activator or streptokinase.

Most proteins introduced into the circulation, are cleared quickly from the mammalian subject by the kidneys. This problem may be partially overcome by administering a larger amount of the protein or through repeated administration. However, higher doses of the protein can elicit antibodies which can bind and inactivate the protein and/or facilitate the clearance of the protein from the subject's body. Repeated administration of the therapeutic protein is essentially ineffective and can be dangerous as it can elicit an allergic response.

Various attempts to solve the problems associated with protein therapies include microencapsulation, liposome delivery systems, administration of fusion proteins, and chemical modification. The most promising of these to date is modification of the therapeutic protein by covalent attachment of polyalkylene oxide polymers, particularly polyethylene glycols (PEG). For example, U.S. Pat. No. 4,179,337 discloses the use of PEG or polypropylene glycol coupled to proteins to provide a physiologically active non-immunogenic water soluble polypeptide composition. Nucci et al. describe several proteins which have been modified by addition of PEG including adenosine deaminase, L-asparaginase, interferon alpha 2b (IFN-α2b), superoxide dismutase, streptokinase, tissue plasminogen activator (tPA), urokinase, uricase, hemoglobin, interleukins, interferons, TGF-beta, EGF, and other growth factors (Nucci et al., 1991, *Adv. Drug Delivery Rev.* 4:133–151). Attempts such as these have resulted in somewhat longer half-life of the proteins and reduction of protein immunogenicity.

Typically, PEGylation of proteins involves activating PEG with a functional group which will react with lysine residues on the surface of the protein. If the modification of the protein goes to completion, the activity of the protein is usually lost. Modification procedures which allow partial PEGylation of the protein usually result in only about 50% loss of activity and greatly increased serum half-life, so that the overall effective dose of the protein is lower.

Recent developments in protein PEGylation methods employ activated PEG reagents which react with thiol groups of the protein, resulting in covalent attachment of PEG to a cysteine, which residue was inserted in place of a naturally occurring lysine of the protein. Shaw et al. (U.S. Pat. No. 5,166,322) describe specific variants of IL-3 which have a cysteine introduced at specific sites within the naturally occurring amino acid sequence. Sulfhydryl reactive compounds (e.g. activated polyethylene glycol) are then attached to these cysteines by reaction with the IL-3 variant. Katre et al. (U.S. Pat. No. 5,206,344) describe specific IL-2 variants which contain a cysteine introduced at a specific site within the naturally occurring amino acid sequence. The IL-2 variant is subsequently reacted with an activated polyethylene glycol reagent to attach this moiety to a cysteine.

There is still a need in the art for improved Factor VII polypeptides having prolonged procoagulant or anticoagulant activity. In particular, there is a need for Factor VII polypeptides which has increased serum half-life without the undesirable side effects such as systemic activation of the coagulation system and bleeding, respectively, associated with conventional therapies, and which can be administered at relatively low doses so that repeated administrations of a larger amount of the protein are avoided.

DESCRIPTION OF THE INVENTION

The present invention relates to novel coagulation Factor VII polypeptides with the same or increased activity compared to wild type Factor VIIa and to Factor VII derivatives having increased serum half-lifes.

Areas in the Factor VIIa molecule has been identified where changes to the primary structure as well as other modifications are allowed without influencing or reducing the biological activity of Factor VIIa. The areas within the structure of Factor VIIa, which have been identified not to be involved in the binding to tissue factor or to Factor X, includes the amino acid positions from 247–260 and from 393–406 of SEQ ID NO: 1. Specifically the amino acids in positions Q250, R396, and P406 of the sequence of SEQ ID NO: 1, have been analysed for the introduction of cysteine (Cys) residues. The introduction of a Cys residues is followed by the conjugation with a chemical group, e.g. polyethylene glycol (PEG) in order to increase the half-life in circulation of the Factor VII derivative. A cysteine has also been introduced in the C-terminal sequence of SEQ ID NO: 1 (referred to as 407C), which is followed by the conjugation of PEG. Also this addition of a cysteine in the C-terminal sequence of SEQ ID NO: 1 is without reduction in proteolytic activity of Factor VIIa polypeptides. These Factor VII derivatives, e.g. a Factor VII polypeptide conjugated with a PEG molecule, are therapeutically useful in situations where a prolonged effect of Factor VII polypeptides is desirable, e.g. in situations where repeated administration or administration of a larger amount of the Factor VII polypeptide is inconvenient or problematic. Furthermore, the Factor VIIa polypeptides of the present invention with introduced amino acids (e.g. a Cys residue) capable of being conjugated with a chemical group at positions in the Factor VIIa molecule, which do no influence the proteolytic activity, may be used to introduce any functional group of a conjugate of Factor VII.

In a first aspect, the present invention relates to a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa.

In a second aspect, the invention relates to a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid. It is to be understood that any amino acid at a position selected from 247–260, 393–405 or 406 of SEQ ID NO: 1 can be substituted with a different amino acid without substantially reduction in activity of the Factor VII polypeptide.

In a third aspect, the invention relates to a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid. It is to be understood, that the first letter in R396, Q250 and P406 represent the amino acid naturally present at the indicated position of SEQ ID NO: 1.

In a further aspect, the invention relates to a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa. It is to be understood, that the amino acid may be inserted within the sequence of SEQ ID NO: 1, without replacing any amino acid. The insertion of an amino acid may be at the same position within the sequence of SEQ ID NO: 1, where an amino acid is further substituted. Thus, in one embodiment the amino acid insertion is followed by an amino acid substitution or vice versa.

In a further aspect, the invention relates to a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof.

The term "an amino acid" as used herein means one or more amino acids. It is to be understood that the amino acid replacing the amino acid in or being inserted into or being added to the Factor VII polypeptide is capable of being conjugated with any chemical group that will increase the actual molecular weight of the Factor VII polypeptide. This conjugation with the chemical group includes but are not limited to covalent attachment of polyethylene glycol (PEG), monomethoxy-polyethylene glycol, dextran, poly-(N-vinyl pyrrolidone) polyethylene glycol, propylene glycol homopolymers, a polypropylene oxide/ethylene oxide copolymer, polypropylene glycol, polyoxyethylated polyols (e.g., glycerol) and polyvinyl alcohol, colominic acids or other carbohydrate based polymers, polymers of amino acids, and biotin derivatives.

Preferably the chemical group is a biocompatible, non-toxic, non-immunogenic and water-soluble polymer. Preferably the chemical group is water-soluble in all proportions.

This amino acid substitution, insertion, or addition and conjugation with a chemical group is without substantial reduction of procoagulant activity of the activated form of the Factor VII derivative compared with recombinant wild type human Factor VIIa.

The term "Factor VII polypeptide" as used herein means any protein comprising the amino acid sequence 1–406 of native human Factor VII (SEQ ID NO: 1) or variants thereof. This includes but are not limited to human Factor VII, human Factor VIIa and variants thereof.

The terms "factor VII", or "FVII" as used herein means a product consisting of the unactivated form (factor VII). The term "factor VIIa", or "FVIIa" as used herein means a product consisting of the activated form (factor VIIa). This includes proteins that have the amino acid sequence 1–406 of native human Factor VII or Factor VIIa. It also includes proteins with a slightly modified amino acid sequence, for instance, a modified N-terminal end including N-terminal amino acid deletions or additions so long as those proteins substantially retain the activity of Factor VIIa. "Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

The terms "variant" or "variants", as used herein, is intended to designate human Factor VII having the sequence of SEQ ID NO: 1, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both.

The term "substantially the same activity or increased activity compared to recombinant wild type human Factor VIIa", as used herein, means an activity more than 70% of the activity of recombinant wild type human Factor VIIa. In one embodiment the activity is more than 80% of the activity of recombinant wild type human Factor VIIa. In another embodiment the activity is more than 90% of the activity of recombinant wild type human Factor VIIa. In a further embodiment the activity is more than 100% of the activity of recombinant wild type human Factor VIIa. In a further embodiment the activity is more than 120% of the activity of recombinant wild type human Factor VIIa. In a further embodiment the activity is more than 200% of the activity of recombinant wild type human Factor VIIa. In a further embodiment the activity is more than 400% of the activity of recombinant wild type human Factor VIIa.

The term "Factor VII derivative" as used herein, is intended to designate a Factor VII polypeptide having the sequence of SEQ ID NO: 1 or a variant thereof, in which one or more of the amino acids of the parent peptide have been chemically modified, e.g. by alkylation, PEGy-lation, acy-lation, ester formation or amide formation or the like. This includes but are not limited to PEGylated human Factor VIIa, cysteine-PEGylated human Factor VIIa and variants thereof.

The term "PEGylated human Factor VIIa" means Factor VIIa, having a PEG molecule conjugated to an amino acid of the human Factor VIIa polypeptide.

The term "cysteine-PEGylated human Factor VIIa" means Factor VIIa having a PEG molecule conjugated to a sulfhydryl group of a cysteine introduced in human Factor VIIa.

The term "a different amino acid" as used herein means one or more amino acids that are different from that amino acid naturally present at that position. This includes but are not limited to amino acids that can be encoded by a polynucleotide. Preferably the different amino acid is in natural L-form and can be encoded by a polynucleotide. A specific example being L-cysteine (Cys).

The term "activity" as used herein means the ability of a Factor VII polypeptide to convert its substrate Factor X to the active Factor Xa. The activity of a Factor VII polypeptide may be measured with the "In Vitro Proteolysis Assay" (see Example 6).

The term "polyethylene glycol" or "PEG" means a polyethylene glycol compound or a derivative thereof, with or without coupling agents, coupling or activating moeities (e.g., with thiol, triflate, tresylate, azirdine, oxirane, or preferably with a maleimide moiety). Compounds such as maleimido monomethoxy PEG are exemplary of activated PEG compounds of the invention.

In a further aspect, the invention relates to a Factor VII derivative comprising a Factor VII polypeptide having the amino acid sequence of SEQ ID NO: 1 or a variant thereof, wherein an amino acid has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

The term "a chemical group" as used herein means one or more chemical groups.

In a further aspect, the invention relates to a Factor VII derivative comprising a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a Factor VII derivative comprising a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a Factor VII derivative comprising a Factor VII polypeptide having the amino acid sequence of SEQ ID NO: 1 or a variant thereof, wherein an amino acid has been inserted within the sequence of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a Factor VII derivative comprising a Factor VII polypeptide having the amino acid sequence of SEQ ID NO: 1 or a variant thereof, wherein an amino acid has been added to the N- or C-terminal of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a composition comprising a Factor VII derivative comprising a Factor VII polypeptide having the amino acid sequence of SEQ ID NO: 1 or a variant thereof, wherein an amino acid has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a composition comprising a Factor VII derivative comprising a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a composition comprising a Factor VII derivative comprising a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a composition comprising a Factor VII derivative comprising a Factor VII polypeptide having the amino acid sequence of SEQ ID NO: 1 or a variant thereof, wherein an amino acid has been inserted within the sequence of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a composition comprising a Factor VII derivative comprising a Factor VII polypeptide having the amino acid sequence of SEQ ID NO: 1 or a variant thereof, wherein an amino acid has been added to the N- or C-terminal of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a pharmaceutical composition comprising a Factor VII derivative comprising a Factor VII polypeptide having the amino acid sequence of SEQ ID NO: 1 or a variant thereof, wherein an amino acid has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa; and optionally, a pharmaceutically acceptable carrier.

In a further aspect, the invention relates to a pharmaceutical composition comprising a Factor VII derivative comprising a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa; and optionally, a pharmaceutically acceptable carrier.

In a further aspect, the invention relates to a pharmaceutical composition comprising a Factor VII derivative comprising a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa; and optionally, a pharmaceutically acceptable carrier.

In a further aspect, the invention relates to a pharmaceutical composition comprising a Factor VII derivative comprising a Factor VII polypeptide having the amino acid sequence of SEQ ID NO: 1 or a variant thereof, wherein an amino acid has been inserted within the sequence of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa; and optionally, a pharmaceutically acceptable carrier.

In a further aspect, the invention relates to a pharmaceutical composition comprising a Factor VII derivative comprising a Factor VII polypeptide having the amino acid sequence of SEQ ID NO: 1 or a variant thereof, wherein an amino acid has been added to the N- or C-terminal of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa; and optionally, a pharmaceutically acceptable carrier. In a further aspect, the invention relates to an inactivated Factor VII polypeptide, wherein a Factor VII polypeptide is further modified in its catalytic center, which modification inhibits the ability of the Factor VII polypeptide to activate plasma Factor X or IX. In one embodiment the inactivated Factor VII polypeptide is modified in its catalytic center with a serine protease inhibitor. In a further embodiment the inactivated Factor VII polypeptide is modified in its catalytic center with a peptide halomethyl ketone selected from the group consisting of: Phe-Phe-Arg chloromethyl ketone, Phe-Phe-Arg chloromethylketone, D-Phe-Phe-Arg chloromethyl ketone, D-Phe-Phe-Arg chloromethylketone Phe-Pro-Arg chloromethylketone, D-Phe-Pro-Arg chloromethylketone, Phe-Pro-Arg chloromethylketone, D-Phe-Pro-Arg chloromethylketone, L-Glu-Gly-Arg chloromethylketone and D-Glu-Gly-Arg chloromethylketone, Dansyl-Phe-Phe-Arg chloromethyl ketone, Dansyl-Phe-Phe-Arg chloromethylketone, Dansyl-D-Phe-Phe-Arg chloromethyl ketone, Dansyl-D-Phe-Phe-Arg chloromethylketone, Dansyl-Phe-Pro-Arg chloromethylketone, Dansyl-D-Phe-Pro-Arg chloromethylketone, Dansyl-Phe-Pro-Arg chloromethylketone, Dansyl-D-Phe-Pro-Arg chlorometh-ylketone, Dansyl-L-Glu-Gly-Arg chloromethylketone and Dansyl-D-Glu-Gly-Arg chloromethylketone.

The term "inactivated Factor VII polypeptide" as used herein means a Factor VII polypeptide with no ability to activate plasma Factor X or IX.

In a further aspect, the invention relates to an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to an inactivated Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a composition comprising an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX is further conjugated with a chemical group that increases the actual molecular weight of the inactivated Factor VII polypeptide with about 300 daltons to about 100,000 daltons.

In a further aspect, the invention relates to a composition comprising an inactivated Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a composition comprising an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a composition comprising an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a composition comprising an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a composition comprising an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a pharmaceutical composition comprising an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX is further conjugated with a chemical group that increases the actual molecular weight of the inactivated Factor VII polypeptide with about 300 daltons to about 100,000 daltons; and optionally, a pharmaceutically acceptable carrier.

In a further aspect, the invention relates to a pharmaceutical composition comprising an inactivated Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons; and optionally, a pharmaceutically acceptable carrier.

In a further aspect, the invention relates to a pharmaceutical composition comprising an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons; and optionally, a pharmaceutically acceptable carrier.

In a further aspect, the invention relates to a pharmaceutical composition comprising an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons; and optionally, a pharmaceutically acceptable carrier.

In a further aspect, the invention relates to a pharmaceutical composition comprising an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons; and optionally, a pharmaceutically acceptable carrier.

In a further aspect, the invention relates to a pharmaceutical composition comprising an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons; and optionally, a pharmaceutically acceptable carrier.

In a further aspect, the invention relates to a polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa.

In a further aspect, the invention relates to a polynucleotide construct encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid.

In a further aspect, the invention relates to a polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid.

In a further aspect, the invention relates to a polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa.

In a further aspect, the invention relates to a polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof.

In one embodiment the polynucleotide construct is a vector.

The term "a polynucleotide" denotes a single- or double-stranded polymer of deoxy-ribonucleotide or ribonucleotide bases read from the 5' to the 3' end. Polynucleotides include RNA and DNA, and may be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term "nucleotides" is used for both single- and double-stranded molecules where the context permits. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

The term "vector", as used herein, means any nucleic acid entity capable of the amplification in a host cell. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contains a replication origin and at least one selectable gene, i.e., a gene which encodes a product which is readily detectable or the presence of which is essential for cell growth.

In a further aspect, the invention relates to a eucaryotic host cell comprising a polynucleotide construct comprising a sequence encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa.

In a further aspect, the invention relates to a eucaryotic host cell comprising a polynucleotide construct comprising a sequence encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid.

In a further aspect, the invention relates to a eucaryotic host cell comprising a polynucleotide construct comprising a sequence encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid.

In a further aspect, the invention relates to a eucaryotic host cell comprising a polynucleotide construct comprising a sequence encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa.

In a further aspect, the invention relates to a eucaryotic host cell comprising a polynucleotide construct comprising a sequence encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof.

The term "a eucaryotic host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK) and HEK293 (e.g., ATCC CRL 1573; Graham et al., *J. Gen. Virol.* 36:59–72, 1977) cell lines.

A preferred BHK cell line is the tk⁻ ts13 BHK cell line (Waechter and Baserga, *Proc. Natl. Acad. Sci. USA* 79:1106–1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216–4220,1980). Also useful are 3T3 cells, Namalwa cells, myelomas and fusions of myelomas with other cells. In one embodiment the eucaryotic host cell is of mammalian origin. In a further embodiment the eucaryotic host cell is selected from the group consisting of CHO cells, BHK cells or HEK cells.

In a further aspect, the invention relates to a transgenic animal expressing the polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa.

In a further aspect, the invention relates to a transgenic animal expressing the polynucleotide construct encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid.

In a further aspect, the invention relates to a transgenic animal expressing the polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid.

In a further aspect, the invention relates to a transgenic animal expressing the polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa.

In a further aspect, the invention relates to a transgenic animal expressing the polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof.

In a further aspect, the invention relates to a transgenic plant expressing the polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa.

In a further aspect, the invention relates to a transgenic plant expressing the polynucleotide construct encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid.

In a further aspect, the invention relates to a transgenic plant expressing the polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid.

In a further aspect, the invention relates to a transgenic plant expressing the polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa.

In a further aspect, the invention relates to a transgenic plant expressing the polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof.

In a further aspect, the invention relates to a method for producing a Factor VII polypeptide, the method comprising cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa under conditions allowing protein synthesis from the polynucleotide construct and recovering the Factor VII polypeptide from the culture medium.

In a further aspect, the invention relates to a method for producing a Factor VII polypeptide, the method comprising cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid under conditions allowing protein synthesis from the polynucleotide construct and recovering the Factor VII polypeptide from the culture medium.

In a further aspect, the invention relates to a method for producing a Factor VII polypeptide, the method comprising cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid under conditions allowing protein synthesis from the polynucleotide construct and recovering the Factor VII polypeptide from the culture medium.

In a further aspect, the invention relates to a method for producing a Factor VII polypeptide, the method comprising cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa under conditions allowing protein synthesis from the polynucleotide construct and recovering the Factor VII polypeptide from the culture medium.

In a further aspect, the invention relates to a method for producing a Factor VII polypeptide, the method comprising cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof under conditions allowing protein synthesis from the polynucleotide construct and recovering the Factor VII polypeptide from the culture medium.

In a further aspect, the invention relates to a method for producing a Factor VII polypeptide, the method comprising recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa.

In a further aspect, the invention relates to a method for producing a Factor VII polypeptide, the method comprising recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid corresponding to an amino acid at a position selected from 247–260, 393405 or 406 of SEQ ID NO: 1 has been substituted with a different amino acid.

In a further aspect, the invention relates to a method for producing a Factor VII polypeptide, the method comprising recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid.

In a further aspect, the invention relates to a method for producing a Factor VII polypeptide, the method comprising recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa.

In a further aspect, the invention relates to a method for producing a Factor VII polypeptide, the method comprising recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof.

In a further aspect, the invention relates to a method for producing a Factor VII polypeptide, the method comprising cultivating a cell of a transgenic plant expressing a polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa, and recovering the Factor VII polypeptide from the transgenic plant.

In a further aspect, the invention relates to a method for producing a Factor VII polypeptide, the method comprising cultivating a cell of a transgenic plant expressing a polynucleotide construct encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, and recovering the Factor VII polypeptide from the transgenic plant.

In a further aspect, the invention relates to a method for producing a Factor VII polypeptide, the method comprising cultivating a cell of a transgenic plant expressing a polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, and recovering the Factor VII polypeptide from the transgenic plant.

In a further aspect, the invention relates to a method for producing a Factor VII polypeptide, the method comprising cultivating a cell of a transgenic plant expressing a polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa, and recovering the Factor VII polypeptide from the transgenic plant.

In a further aspect, the invention relates to a method for producing a Factor VII polypeptide, the method comprising cultivating a cell of a transgenic plant expressing a polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof, and recovering the Factor VII polypeptide from the transgenic plant.

In a further aspect, the invention relates to a method for producing a Factor VII derivative comprising the steps of:
a) producing a Factor VII polypeptide;
b) conjugating the Factor VII polypeptide with a chemical group;
c) applying the Factor VII derivative to a cation exchange chromatography or gelfiltration column; and
d) eluting the Factor VII derivative.

In a further aspect, the invention relates to a method of producing an inactivated Factor VII derivative comprising the steps of:
a) producing a Factor VII polypeptide;
b) modifying the Factor VII polypeptide in its catalytic center with a serine protease inhibitor.
c) conjugating the inactivated Factor VII polypeptide with a chemical group;
d) applying the inactivated Factor VII derivative to a cation exchange chromatography or gelfiltration column; and
e) eluting the inactivated Factor VII derivative.

In one embodiment of the invention the method for producing the Factor VII polypeptide comprises cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa under conditions allowing protein synthesis from the polynucleotide construct and recovering the Factor VII polypeptide from the culture medium.

In a further embodiment of the invention the method for producing the Factor VII polypeptide comprises cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid under conditions allowing protein synthesis from the polynucleotide construct and recovering the Factor VII polypeptide from the culture medium.

In a further embodiment of the invention the method for producing the Factor VII polypeptide comprises cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid under conditions allowing protein synthesis from the polynucleotide construct and recovering the Factor VII polypeptide from the culture medium.

In a further embodiment of the invention the method for producing the Factor VII polypeptide comprises cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa under conditions allowing protein synthesis from the polynucleotide construct and recovering the Factor VII polypeptide from the culture medium.

In a further embodiment of the of the invention the method for producing the Factor VII polypeptide comprises cultivating in an appropriate growth medium a eucaryotic host cell comprising the polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof under conditions allowing protein synthesis from the polynucleotide construct and recovering the Factor VII polypeptide from the culture medium.

In a further embodiment of the invention the method for producing the Factor VII polypeptide comprises recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa.

In a further embodiment of the invention the method for producing the Factor VII polypeptide comprises recovering the Factor VII polypeptide from milk produced by a transgenic animal expressing a polynucleotide construct encoding a Factor VII polypeptide comprising the amino acid sequence of SEQ ID NO: 1 or a variant therof, wherein an amino acid corresponding to an amino acid at a position selected from 247–260, 393–405 or 406 of SEQ ID NO: 1 has been substituted with a different amino acid.

In a further embodiment of the invention the method for producing the Factor VII polypeptide comprises recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid.

In a further embodiment of the invention the method for producing the Factor VII polypeptide comprises recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa.

In a further embodiment of the invention the method for producing the Factor VII polypeptide comprises recovering the Factor VII polypeptide from milk produced by a transgenic animal expressing a polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof.

In a further embodiment of the invention the method for producing the Factor VII polypeptide comprises cultivating a cell of a transgenic plant expressing the polynucleotide construct encoding a Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa, and recovering the Factor VII polypeptide from the transgenic plant.

In a further embodiment of the invention the method for producing the Factor VII polypeptide comprises cultivating a cell of a transgenic plant expressing a polynucleotide construct encoding a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, and recovering the Factor VII polypeptide from the transgenic plant.

In a further embodiment of the invention the method for producing the Factor VII polypeptide comprises cultivating a cell of a transgenic plant expressing a polynucleotide construct encoding a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, and recovering the Factor VII polypeptide from the transgenic plant.

In a further embodiment of the invention the method for producing the Factor VII polypeptide comprises cultivating a cell of a transgenic plant expressing a polynucleotide construct encoding a Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa, and recovering the Factor VII polypeptide from the transgenic plant.

In a further embodiment of the invention the method for producing the Factor VII polypeptide comprises cultivating a cell of a transgenic plant expressing a polynucleotide construct encoding a Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof, and recovering the Factor VII polypeptide from the transgenic plant.

In a further aspect, the invention relates to the use of a Factor VII derivative comprising a Factor VII polypeptide having the amino acid sequence of SEQ ID NO: 1 or a variant thereof, wherein an amino acid has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

The term "treatment", as used herein, means the administration of an effective amount of a therapeutically active compound of the invention with the purpose of preventing any symptoms or disease state to develop or with the purpose of curing or easing such symptoms or disease states already developed. The term "treatment" is thus meant to include prophylactic treatment.

The term "enhancement of the normal haemostatic system" means an enhancement of the ability to generate thrombin.

As used herein the term "bleeding disorders" reflects any defect, congenital, acquired or induced, of cellular or molecular origin that is manifested in bleedings. Examples are clotting factor deficiencies (e.g. haemophilia A and B or deficiency of coagulation Factors XI or VII), clotting factor inhibitors, defective platelet function, thrombocytopenia or von Willebrand's disease.

The term "bleeding episodes" is meant to include uncontrolled and excessive bleeding which is a major problem both in connection with surgery and other forms of tissue damage. Uncontrolled and excessive bleeding may occur in subjects having a normal coagulation system and subjects having coagulation or bleeding disorders. Clotting factor deficiencies (haemophilia A and B, deficiency of coagulation factors XI or VII) or clotting factor inhibitors may be the cause of bleeding disorders. Excessive bleedings also occur in subjects with a normally functioning blood clotting cascade (no clotting factor deficiencies or -inhibitors against any of the coagulation factors) and may be caused by a defective platelet function, thrombocytopenia or von Willebrand's disease. In such cases, the bleedings may be similar to those bleedings caused by haemophilia because the haemostatic system, as in haemophilia, lacks or has abnormal essential clotting "compounds" (such as platelets or von Wille-brand factor protein) that causes major bleedings. In subjects who experience extensive tissue damage in association with surgery or vast trauma, the normal haemostatic mechanism may be overwhelmed by the demand of immediate haemostasis and they may develop bleeding in spite of a normal haemostatic mechanism. Achieving satisfactory haemostasis also is a problem when bleedings occur in organs such as the brain, inner ear region and eyes with limited possibility for surgical haemostasis. The same problem may arise in the process of taking biopsies from various organs (liver, lung, tumour tissue, gastrointestinal tract) as well as in laparoscopic surgery. Common for all these situations is the difficulty to provide haemostasis by surgical techniques (sutures, clips, etc.) which also is the case when bleeding is diffuse (haemorrhagic gastritis and profuse uterine bleeding). Acute and profuse bleedings may also occur in subjects on anticoagulant therapy in whom a defective haemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical haemostasis, and which may result in diffuse bleeding from a large area. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In a further aspect, the invention relates to the use of a Factor VII derivative comprising a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to the use of a Factor VII derivative comprising a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to the use of a Factor VII derivative comprising a Factor VII polypeptide having the amino acid sequence of SEQ ID NO: 1 or a variant thereof, wherein an amino acid has been inserted within the sequence of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to the use of a Factor VII derivative comprising a Factor VII polypeptide having the amino acid sequence of SEQ ID NO: 1 or a variant thereof, wherein an amino acid has been added to the N- or C-terminal of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In one embodiment of the invention, the bleeding is associated with haemophilia A or B. In another embodiment, the bleeding is associated with haemophilia with aquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with haemorrhagic gastritis. In another embodiment, the bleeding is profuse uterine bleeding. In another embodiment, the bleeding is occurring in organs with a limited possibility for mechanical haemostasis. In another embodiment, the bleeding is occurring in the brain, inner ear region or eyes. In another embodiment, the bleeding is associated with the process of taking biopsies. In another embodiment, the bleeding is associated with anticoagulant therapy.

The term "subject" as used herein is intended to mean any animal, in particular mammals, such as humans, and may, where appropriate, be used interchangeably with the term "patient".

In a further aspect, the invention relates to the use of a Factor VII derivative comprising a Factor VII polypeptide having the amino acid sequence of SEQ ID NO: 1 or a variant thereof, wherein an amino acid has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to the use of a Factor VII derivative comprising a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to the use of a Factor VII derivative comprising a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to the use of a Factor VII derivative comprising a Factor VII polypeptide having the amino acid sequence of SEQ ID NO: 1 or a variant thereof, wherein an amino acid has been inserted within the sequence of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to the use of a Factor VII derivative comprising a Factor VII polypeptide having the amino acid sequence of SEQ ID NO: 1 or a variant thereof, wherein an amino acid has been added to the N- or C-terminal of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa for the preparation of a medicament for the treatment of bleeding episodes or for the enhancement of the normal haemostatic system.

In a further aspect, the invention relates to a method for the treatment of bleeding episodes or bleeding disorders in a subject or for the enhancement of the normal haemostatic system, the method comprising administering to a subject in need thereof a therapeutically or prophylactically effective amount of a Factor VII derivative comprising a Factor VII polypeptide having the amino acid sequence of SEQ ID NO: 1 or a variant thereof, wherein an amino acid has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a method for the treatment of bleeding episodes or bleeding disorders in a subject or for the enhancement of the normal haemostatic system, the method comprising administering to a subject in need thereof a therapeutically or prophylactically effective amount of a Factor VII derivative comprising a Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a method for the treatment of bleeding episodes or bleeding disorders in a subject or for the enhancement of the normal haemostatic system, the method comprising administering to a subject in need thereof a therapeutically or prophylactically effective amount of a Factor VII derivative comprising a Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid, wherein the different amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a method for the treatment of bleeding episodes or bleeding disorders in a subject or for the enhancement of the normal haemostatic system, the method comprising administering to a subject in need thereof a therapeutically or prophylactically effective amount of a Factor VII derivative comprising a Factor VII polypeptide having the amino acid sequence of SEQ ID NO: 1 or a variant thereof, wherein an amino acid has been inserted within the sequence of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to a method for the treatment of bleeding episodes or bleeding disorders in a subject or for the enhancement of the normal haemostatic system, the method comprising administering to a subject in need thereof a therapeutically or prophylactically effective amount of a Factor VII derivative comprising a Factor VII polypeptide having the amino acid sequence of SEQ ID NO: 1 or a variant thereof, wherein an amino acid has been added to the N- or C-terminal of SEQ ID NO: 1 or a variant thereof and wherein the amino acid is conjugated with a chemical group that increases the actual molecular weight of the Factor VII polypeptide with about 300 daltons to about 100,000 daltons and wherein the Factor VII derivative has substantially the same activity or increased activity compared to recombinant wild type human Factor VIIa.

In a further aspect, the invention relates to the use of an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons for the preparation of a medicament for inhibiting thrombus formation in a patient.

In a further aspect, the invention relates to the use of an inactivated Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons for the preparation of a medicament for inhibiting thrombus formation in a patient.

In a further aspect, the invention relates to the use of an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons for the preparation of a medicament for inhibiting thrombus formation in a patient.

In a further aspect, the invention relates to the use of an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons for the preparation of a medicament for inhibiting thrombus formation in a patient.

In a further aspect, the invention relates to the use of an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons for the preparation of a medicament for inhibiting thrombus formation in a patient.

In a further aspect, the invention relates to the use of an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated with a chemical group that increases the actual molecularweight of the inactivated Factor VII polypeptide with about 300 daltons to about 100,000 daltons for the preparation of a medicament for inhibiting thrombus formation in a patient.

In a further aspect, the invention relates to a method for inhibiting thrombus formation in a patient comprising administering topically to a vascular site susceptible to thrombus formation in the patient a therapeutically effective dose of a composition comprising an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a method for inhibiting thrombus formation in a patient comprising administering topically to a vascular site susceptible to thrombus formation in the patient a therapeutically effective dose of a composition comprising an inactivated Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a method for inhibiting thrombus formation in a patient comprising administering topically to a vascular site susceptible to thrombus formation in the patient a therapeutically effective dose of a composition comprising an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247–260, 393–405 or 406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a method for inhibiting thrombus formation in a patient comprising administering topically to a vascular site susceptible to thrombus formation in the patient a therapeutically effective dose of a composition comprising an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a method for inhibiting thrombus formation in a patient comprising administering topically to a vascular site susceptible to thrombus formation in the patient a therapeutically effective dose of a composition comprising an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VII and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In a further aspect, the invention relates to a method for inhibiting thrombus formation in a patient comprising administering topically to a vascular site susceptible to thrombus formation in the patient a therapeutically effective dose of a composition comprising an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons.

In one embodiment of the invention the chemical group is substantially neutral.

The term "neutral" as used herein refers to the chemical group being biocompatible, meaning that it is non-toxic, non-immunogenic and water-soluble. Chemical groups being substantially neutral within this definition includes but are not limited to polyethylene glycol (PEG), monomethoxy-polyethylene glycol, dextran, poly-(N-vinyl pyrrolidone) polyethylene glycol, propylene glycol homopolymers, a polypropylene oxide/ethylene oxide co-polymer, polypropylene glycol, polyoxyethylated polyols (e.g., glycerol) and polyvinyl alcohol, colominic acids or other carbohydrate based polymers, polymers of amino acids, and biotin derivatives.

In a further embodiment of the invention the chemical group is water-soluble.

In a further embodiment of the invention the chemical group has a molecular weight of about 1,000 daltons to about 80,000 daltons.

In a further embodiment of the invention the chemical group has a molecular weight of about 5,000 daltons to about 60,000 daltons.

In a further embodiment of the invention the chemical group has a molecular weight of about 10,000 daltons to about 40,000 daltons.

In a further embodiment of the invention the chemical group has a molecular weight of about 500 daltons to about 20,000 daltons.

In a further embodiment of the invention the chemical group has a molecular weight of about 500 daltons to about 5000 daltons.

In a further embodiment of the invention the chemical group has a molecular weight of about 750 daltons to about 5000 daltons.

In a further embodiment of the invention the chemical group is polyethylene glycol.

In a further embodiment of the invention the chemical group is selected from one to six molecules of polyethylene glycol.

In a preferred embodiment of the invention the chemical group is one molecule of polyethylene glycol.

In a further embodiment of the invention the chemical group is monomethoxy-polyethylene glycol.

In a further embodiment of the invention the chemical group is dextran.

In a further embodiment of the invention the chemical group is poly-(N-vinyl pyrrolidone) polyethylene glycol.

In a further embodiment of the invention the chemical group is propylene glycol homopolymers.

In a further embodiment of the invention the chemical group is polypropylene oxide.

In a further embodiment of the invention the chemical group is polypropylene glycol.

In a further embodiment of the invention the chemical group is a polyoxyethylated polyol.

In a further embodiment of the invention the chemical group is polyvinyl alcohol.

In a further embodiment of the invention the chemical group is colominic acid.

In a further embodiment of the invention the chemical group is a carbohydrate based polymer.

In a further embodiment of the invention the chemical group is a polymer of amino acids.

In a further embodiment of the invention the chemical group is a biotin derivative.

In a further embodiment of the invention the chemical group is conjugated to a free sulfhydryl group present on the amino acid substituted for an amino acid in, inserted in or added to the polypeptide.

In a further embodiment of the invention the chemical group is conjugated to a cysteine.

In one embodiment of the invention, the substituted, inserted or added amino acid is capable of being conjugated with a chemical group.

In a further embodiment of the invention the amino acid capable of being conjugated with a chemical group is an amino acid with a free sulfhydryl group.

In a further embodiment of the invention the amino acid capable of being conjugated with a chemical group is a cysteine.

In a further embodiment of the invention, the substituted, inserted or added amino acid is a sulfhydryl containing amino acid such as a cysteine.

In a further embodiment of the Factor VII polypeptide an amino acid has been inserted at a position selected from 247–260, 393–405 or 406 of SEQ ID NO: 1.

In a further embodiment of the Factor VII polypeptide, the amino acid corresponding to R396 of SEQ ID NO: 1 has been substituted with a different amino acid.

In a further embodiment of the Factor VII polypeptide, the amino acid corresponding to Q250 of SEQ ID NO: 1 has been substituted with a different amino acid.

In a further embodiment of the Factor VII polypeptide, the amino acid corresponding to P406 of SEQ ID NO: 1 has been substituted with a different amino acid.

In a further embodiment of the Factor VII polypeptide an additional amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa.

In a further embodiment of the Factor VII polypeptide a further amino acid capable of being conjugated with a chemical group has been added to the N- or C-terminal of SEQ ID NO: 1 or a variant thereof.

In a further embodiment of the Factor VII polypeptide an amino acid has been added to the C-terminal of SEQ ID NO: 1.

In a further embodiment of the Factor VII polypeptide an amino acid has been added to the N-terminal of SEQ ID NO: 1.

In a further embodiment of the Factor VII polypeptide a cysteine has been added.

In a further embodiment of the Factor VII polypeptide a cysteine has been inserted.

In a further embodiment of the Factor VII polypeptide an amino acid selected from the group consisting of K157, V158, E296, M298, L305, D334, S336, K337, and F374 of SEQ ID NO: 1 has been substituted with another amino acid, which amino acid increases the activity compared to recombinant wild type human Factor VIIa.

In a further embodiment of the Factor VII polypeptide the amino acid corresponding to K157 of SEQ ID NO: 1 has been substituted with an amino acid independently selected from G, V, S, T, N, Q, D and E.

In a further embodiment of the Factor VII polypeptide the amino acid corresponding to V158 of SEQ ID NO: 1 has been substituted with an amino acid independently selected from S, T, N, Q, D and E.

In a further embodiment of the Factor VII polypeptide the amino acid corresponding to V158 of SEQ ID NO: 1 has been substituted with an amino acid independently selected from T and D.

In a further embodiment of the Factor VII polypeptide the amino acid corresponding to E296 of SEQ ID NO: 1 has been substituted with an amino acid independently selected from R, K and V.

In a further embodiment of the Factor VII polypeptide the amino acid corresponding to E296 of SEQ ID NO: 1 has been substituted with V.

In a further embodiment of the Factor VII polypeptide the amino acid corresponding to M298 of SEQ ID NO: 1 has been substituted with an amino acid independently selected from R, K, Q and N.

In a further embodiment of the Factor VII polypeptide the amino acid corresponding to M298 of SEQ ID NO: 1 has been substituted with Q.

In a further embodiment of the Factor VII polypeptide the amino acid corresponding to L305 of SEQ ID NO: 1 has been substituted with an amino acid independently selected from A, V, L, I, M, F, W, P, G, S, T, C, Y, N, E, K, R, H, D and Q.

In a further embodiment of the Factor VII polypeptide the amino acid corresponding to L305 of SEQ ID NO: 1 has been substituted with V.

In a further embodiment of the Factor VII polypeptide the amino acid corresponding to D334 of SEQ ID NO: 1 has been substituted with E.

In a further embodiment of the Factor VII polypeptide the amino acid corresponding to S336 of SEQ ID NO: 1 has been substituted with G.

In a further embodiment of the Factor VII polypeptide the amino acid corresponding to K337 of SEQ ID NO: 1 has been substituted with an amino acid independently selected from A, G, V, S, T, N, Q, D and E.

In a further embodiment of the Factor VII polypeptide the amino acid corresponding to K337 of SEQ ID NO: 1 has been substituted with A.

In a further embodiment of the Factor VII polypeptide the amino acid corresponding to F374 of SEQ ID NO: 1 has been substituted with an amino acid independently selected from A, V, L, I, M, F, W, P, G, S, T, C, Y, N, E, K, R, H, D and Q.

In a further embodiment of the Factor VII polypeptide the amino acid corresponding to F374 of SEQ ID NO: 1 has been substituted with P.

In a further embodiment of the invention the Factor VII polypeptide is human Factor VII.

In a further embodiment of the invention the Factor VII polypeptide is human Factor VIIa.

In the present specification, amino acids are represented using abbreviations, as indicated in table 1, approved by IUPAC-IUB Commission on Biochemical Nomenclature (CBN). Amino acid and the like having isomers represented by name or the following abbreviations are in natural L-form unless otherwise indicated. Further, the left and right ends of an amino acid sequence of a peptide are, respectively, the N- and C-termini unless otherwise specified.

TABLE 1

Abbreviations for amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The invention also relates to a method of preparing human Factor VII polypeptides as mentioned above. The human Factor VII polypeptides are preferably produced by recombinant DNA techniques. To this end, DNA sequences encoding human Factor VII may be isolated by preparing a genomic or cDNA library and screening for DNA sequences coding for all or part of the protein by hybridization using synthetic oligonucleotide probes in accordance with standard techniques (cf. Sambrook et al., *Molecular Cloning: A Laboratory Manual*, Cold Spring Harbor Laboratory, Cold Spring Harbor, N.Y., 1989). For the present purpose, the DNA sequence encoding the protein is preferably of human origin, i.e. derived from a human genomic DNA or cDNA library.

The DNA sequences encoding the human Factor VII polypeptides may also be prepared synthetically by established standard methods, e.g. the phosphoamidite method described by Beaucage and Caruthers, *Tetrahedron Leffers* 22 (1981), 1859–1869, or the method described by Matthes et al., *EMBO Journal* 3 (1984), 801–805. According to the phosphoamidite method, oligonucleotides are synthesized, e.g. in an automatic DNA synthesizer, purified, annealed, ligated and cloned in suitable vectors.

The DNA sequences may also be prepared by polymerase chain reaction using specific primers, for instance as described in U.S. Pat. No. 4,683,202, Saiki et al., *Science* 239 (1988), 487–491, or Sambrook et al., supra.

The DNA sequences encoding the human Factor VII polypeptides are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the human Factor VII polypeptides is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

The promoter may be any DNA sequence, which shows transcriptional activity in the host cell of choice and may be derived from genes encoding proteins either homologous or heterologous to the host cell.

Examples of suitable promoters for directing the transcription of the DNA encoding the human Factor VII polypeptide in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814), the CMV promoter (Boshart et al., *Cell* 41:521–530, 1985) or the adenovirus 2 major late promoter (Kaufman and Sharp, *Mol. Cell. Biol*, 2:1304–1319, 1982).

An example of a suitable promoter for use in insect cells is the polyhedrin promoter (U.S. Pat. No. 4,745,051; Vasuvedan et al., *FEBS Lett.* 311, (1992) 7–11), the P10 promoter (J. M. Vlak et al., *J. Gen. Virology* 69, 1988, pp. 765–776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al, eds.), Plenum Press, New York, 1982), or the TPI 1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., The *EMBO J.* 4 (1985), 2093–2099) or the tpiA promoter. Examples of other useful promoters are those derived from the gene encoding *A. oryzae* TAKA amylase, *Rhizomucor miehei* aspartic proteinase, A. niger neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the human Factor VII polypeptides may also, if necessary, be operably connected to a suitable terminator, such as the human growth hormone terminator (Palmiter et al., *Science* 222, 1983, pp. 809–814) or the TPI1 (Alber and Kawasaki, *J. Mol. Appl. Gen.* 1, 1982, pp. 419–434) or ADH3 (McKnight et al., The *EMBO J.* 4, 1985, pp. 2093–2099) terminators. The vector may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. *Nuc. Acids Res.* 9:3719–3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2μ replication genes REP 1–3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD or sC.

To direct the human Factor VII polypeptides of the present invention into the secretory pathway of the host cells, a secretory signal sequence (also known as a leader sequence, prepro sequence or pre sequence) may be provided in the recombinant vector. The secretory signal sequence is joined to the DNA sequences encoding the human Factor VII polypeptides in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed human Factor VII polypeptides into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643–646), a modified carboxypeptidase signal peptide (cf. L. A. Valls et al., *Cell* 48, 1987, pp. 887–897), the yeast BAR1 signal peptide (cf. WO 87/02670), or the yeast aspartic protease 3 (YAP3) signal peptide (cf. M. Egel-Mitani et al., *Yeast* 6, 1990, pp. 127–137).

For efficient secretion in yeast, a sequence encoding a leader peptide may also be inserted downstream of the signal sequence and upstream of the DNA sequence encoding the human Factor VII polypeptides. The function of the leader peptide is to allow the expressed peptide to be directed from the endoplasmic reticulum to the Golgi apparatus and further to a secretory vesicle for secretion into the culture medium (i.e.exportation of the human Factor VII polypeptides across the cell wall or at least through the cellular membrane into the periplasmic space of the yeast cell). The leader peptide may be the yeast alpha-factor leader (the use of which is described in e.g. U.S. Pat. No. 4,546,082, U.S. Pat. No. 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the human Factor VII polypeptides, the promoter and optionally the terminator and/or secretory signal sequence, respectively, and to insert them into suitable vectors containing the information necessary for replication, are well known to persons skilled in the art (cf., for instance, Sambrook et al., *Molecular Cloning: A Laboratory Manual*, Cold Spring Harbor, N.Y., 1989).

Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Genet.* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1–2 days, to begin expressing the gene of interest. As used herein the term "appropriate growth medium" means a medium containing nutrients and other components required for the growth of cells and the expression of the human Factor VII polypeptides of interest. Media generally include a carbon source, a nitrogen source, essential amino acids, essential sugars, vitamins, salts, phospholipids, protein and growth factors. For production of gamma-carboxylated proteins, the medium will contain vitamin K, preferably at a concentration of about 0.1 µg/ml to about 5 µg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the human Factor VII polypeptide of interest.

The host cell into which the DNA sequences encoding the human Factor VII polypeptides is introduced may be any cell, which is capable of producing the posttranslational modified human Factor VII polypeptides and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., *J. Gen. Virol.* 36:59–72, 1977) cell lines. A preferred BHK cell line is the tk⁻ ts13 BHK cell line (Waechter and Baserga, *Proc. Natl. Acad. Sci. USA* 79:1106–1110, 1982, incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk⁻ ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, *Proc. Natl. Acad. Sci. USA* 77:4216–4220, 1980).

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous polypeptides there from are described, e.g. in U.S. Pat. Nos. 4,599,311, 4,931,373, 4,870,008, 5,037,743, and U.S. Pat. No. 4,845, 075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the human Factor VII polypeptides may be preceded by a signal sequence and optionally a leader sequence, e.g. as described above. Further examples of suitable yeast cells are strains of *Kluyveromyces*, such as *K. lactis*, *Hansenula*, e.g. *H. polymorpha*, or *Pichia*, e.g. *P. pastoris* (cf. Gleeson et al., *J. Gen. Microbiol.* 132,1986, pp. 3459–3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae*, *A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, *Gene* 78: 147–156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162,222; EP 397,485) all of which are incorporated herein by reference. The insect cell line used as the host may suitably be a Lepidoptera cell line, such as *Spodoptera frugiperda* cells or *Trchoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the human Factor VII polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The human Factor VII polypeptide produced by the cells may then be recovered from the culture medium by conventional procedures including separating the host cells from the medium by centrifugation or filtration, precipitating the proteinaqueous components of the supernatant or filtrate by means of a salt, e.g. ammonium sulphate, purification by a variety of chromatographic procedures, e.g. ion exchange chromatography, gel-filtration chromatography, affinity chromatography, or the like, dependent on the type of polypeptide in question.

For the preparation of recombinant human Factor VII polypeptides, a cloned wild-type Factor VII DNA sequence is used. This sequence may be modified to encode a desired Factor VII variant. The complete nucleotide and amino acid sequences for human Factor VII are known. See U.S. Pat. No. 4,784,950, which is incorporated herein by reference, where the cloning and expression of recombinant human Factor VII is described. The bovine Factor VII sequence is described in Takeya et al., *J. Biol. Chem,* 263:14868–14872 (1988), which is incorporated by reference herein.

The amino acid sequence alterations may be accomplished by a variety of techniques. Modification of the DNA sequence may be by site-specific mutagenesis. Techniques for site-specific mutagenesis are well known in the art and are described by, for example, Zoller and Smith (*DNA* 3:479–488, 1984). Thus, using the nucleotide and amino acid sequences of Factor VII, one may introduce the alterations of choice.

DNA sequences for use within the present invention will typically encode a pre-pro peptide at the amino-terminus of the Factor VII protein to obtain proper post-translational processing (e.g. gamma-carboxylation of glutamic acid residues) and secretion from the host cell. The pre-pro peptide may be that of Factor VII or another vitamin K-dependent plasma protein, such as factor IX, factor X, prothrombin, protein C or protein S. As will be appreciated by those skilled in the art, additional modifications can be made in the amino acid sequence of Factor VII where those modifications do not significantly impair the ability of the protein to act as a coagulation factor. For example, Factor VII in the catalytic triad can also be modified in the activation cleavage site to inhibit the conversion of zymogen Factor VII into its activated two-chain form, as generally described in U.S. Pat. No. 5,288,629, incorporated herein by reference.

Within the present invention, transgenic animal technology may be employed to produce the human Factor VII polypeptide. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (typically from about 1 to 15 g/l). From a commercial point of view, it is clearly preferable to use as the host a species that has a large milk yield. While smaller animals such as mice and rats can be used (and are preferred at the proof of principle stage), within the present invention it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WIPO Publication WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489, incorporated herein by reference), beta-lactoglobulin, alpha-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as about 4.25 kbp DNA segment encompassing the 5' flanking promoter and non-coding portion of the beta-lactoglobulin gene. See Whitelaw et al., *Biochem J.* 286: 31–39 (1992). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci. USA* 85: 836–840 (1988); Palmiter et al., *Proc. Natl. Acad. Sci. USA* 88: 478–482 (1991); Whitelaw et al., *Transgenic Res.* 1: 3–13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment which provides for intron splicing and RNA polyadenylation from the 3' non-coding region of the ovine beta-lactoglobulin gene. When substituted for the natural 3' non-coding sequences of a gene, this iovine beta-lactoglobulin segment can both enhance and stabilize expression levels of the protein or polypeptide of interest. Within other embodiments, the region surrounding the initiation ATG of the sequence encoding the human Factor VII polypeptide is replaced with corresponding sequences from a milk specific protein gene. Such replacement provides a putative tissue-specific initiation environment to enhance expression. It is convenient to replace the entire pre-pro sequence of the human Factor VII polypeptide and 5' non-coding sequences with those of, for example, the BLG gene, although smaller regions may be replaced.

For expression of a human Factor VII polypeptide in transgenic animals, a DNA segment encoding the human Factor VII polypeptide is operably linked to additional DNA segments required for its expression to produce expression units. Such additional segments include the above-mentioned promoter, as well as sequences which provide for termination of transcription and polyadenylation of mRNA. The expression units will further include a DNA segment encoding a secretory signal sequence operably linked to the segment encoding the human Factor VII polypeptide. The secretory signal sequence may be a native secretory signal sequence of the human Factor VII polypeptide or may be that of another protein, such as a milk protein. See, for example, von Heinje, *Nuc. Acids Res.* 14: 4683–4690 (1986); and Meade et al., U.S. Pat. No. 4,873,316, which are incorporated herein by reference.

Construction of expression units for use in transgenic animals is conveniently carried out by inserting a sequence encoding the human Factor VII polypeptide into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of the human Factor VII polypeptide, thereby creating a gene fusion that includes the expression control sequences of the milk protein gene. In any event, cloning of the expression units in plasmids or other vectors facilitates the amplification of the human Factor VII polypeptide. Amplification is conveniently carried out in bacterial (e.g. *E. coli*) host cells, thus the vectors will typically include an origin of replication and a selectable marker functional in bacterial host cells.

The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, *Science* 240: 1468–1474 (1988)) or site-directed integration using embryonic stem (ES) cells (reviewed by Bradley et al., *Bio/Technology* 10: 534–539 (1992)). The eggs are then implanted into the oviducts or uteri of pseudopregnant females and allowed to develop. Offspring carrying the introduced DNA in their germ line can pass the DNA on to their progeny in the normal, Mendelian fashion, allowing the development of transgenic herds.

General procedures for producing transgenic animals are known in the art. See, for example, Hogan et al., *Manipulating the Mouse Embryo: A Laboratory Manual*, Cold Spring Harbor Laboratory, 1986; Simons et al., *Bio/Technology* 6: 179–183 (1988); Wall et al., Biol. Reprod. 32: 645–651 (1985); Buhler et al., *Bio/Technology* 8: 140–143 (1990); Ebert et al., *Bio/Technology* 9: 835–838 (1991); Krimpenfort et al., *Bio/Technology* 9: 844–847 (1991); Wall et al., *J. Cell. Biochem.* 49:113–120 (1992); U.S. Pat. Nos. 4,873,191 and 4,873,316; WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., *Proc. Natl. Acad. Sci. USA* 77: 7380–7384 (1980); Gordon and Ruddle, *Science* 214: 1244–1246 (1981); Palmiter and Brinster, Cell 41: 343–345 (1985); and Brinsteret al., *Proc. Natl. Acad. Sci. USA* 82: 4438–4442 (1985). These techniques were subsequently adapted for use with larger animals, including livestock species (see e.g., WIPO publications WO 88/00239, WO 90/05188, and WO 92/11757; and Simons et al., *Bio/Technology* 6: 179–183 (1988). To summarize, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed. Production in transgenic plants may also be employed. Expression may be generalized or directed to a particular organ, such as a tuber. See, Hiatt, *Nature* 344:469–479 (1990); Edelbaum et al., *J. Interferon Res.* 12:449–453 (1992); Sijmons et al., *Bio/Technology* 8:217–221 (1990); and European Patent Office Publication EP 265,378.

Factor VII produced according to the present invention may be purified by affinity chromatography on an anti-Factor VII antibody column. It is preferred that the immunoadsorption column comprise a high-specificity monoclonal antibody. The use of calcium-dependent monoclonal antibodies, as described by Wakabayashi et al., *J. Biol. Chem*, 261:11097–11108, (1986) and Thim et al., *Biochem.* 27: 7785–7793, (1988), incorporated by reference herein, is particularly preferred. Additional purification may be achieved by conventional chemical purification means, such as high performance liquid chromatography. Other methods of purification, including barium citrate precipitation, are known in the art, and may be applied to the purification of the Factor VII described herein (see, generally, Scopes, R., *Protein Purification*, Springer-Verlag, N.Y., 1982). Substantially pure Factor VII of at least about 90 to 95% homogeneity is preferred, and 98 to 99% or more homogeneity most preferred, for pharmaceutical uses. Once purified, partially or to homogeneity as desired, the Factor VII may then be used therapeutically.

Conversion of single-chain Factor VII to active two-chain Factor VIIa may be achieved using factor XIIa as described by Hedner and Kisiel (1983, *J. Clin. Invest.* 71: 1836–1841), or with other proteases having trypsin-like specificity (Kisiel and Fujikawa, *Behring Inst Mitt.* 73: 29–42, 1983). Alternatively Factor VII may be autoactivated by passing it through an ion-exchange chromatography column, such as mono Q.RTM. (Pharmacia Fire Chemicals) or the like (Bjoern et al., 1986, *Research Disclosures* 269:564–565). The Factor VII molecules of the present invention and pharmaceutical compositions thereof are particularly useful for administration to humans to treat a variety of conditions involving intravascular coagulation.

The invention also provides suitable assays for selecting preferred Factor VIIa polypeptides and Factor VIIa derivatives according to the invention. These assays can be performed as a simple preliminary in vitro test.

Thus, Example 5 herein discloses a simple test (entitled "In Vitro Hydrolysis Assay") for the activity of Factor VIIa polypeptides of the invention. Based thereon, Factor VIIa polypeptides which are of particular interest are such polypeptides where the ratio between the activity of the variant and the activity of native human Factor VII shown in FIG. 1 is about 1.0 or higher, when tested in the "In Vitro Hydrolysis Assay" defined herein.

The activity of the polypeptides can also be measured using a physiological substrate such as factor X ("In Vitro Proteolysis Assay") (see Example 6), suitably at a concentration of 100–1000 nM, where the factor Xa generated is measured after the addition of a suitable chromogenic substrate (eg. S-2765). In addition, the activity assay may be run at physiological temperature.

The ability of the procoagulant Factor VIIa polypeptides to generate thrombin can also be measured in an assay comprising all relevant coagulation factors and inhibitors at physiological concentrations (minus factor VIII when mimicking haemophilia A conditions) and activated platelets (as described on p. 543 in Monroe et al. (1997) *Brit. J. Haematol.* 99, 542–547 which is hereby incorporated as reference).

The procoagulant Factor VII derivatives according to the present invention may be used to control bleeding disorders which have several causes such as clotting factor deficiencies (e.g. haemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleedings may be caused by a defective platelet function, thrombocytopenia or von Willebrand's disease. They may also be seen in subjects in whom an increased fibrinolytic activity has been induced by various stimuli.

In subjects who experience extensive tissue damage in association with surgery or vast trauma, the haemostatic mechanism may be overwhelmed by the demand of immediate haemostasis and they may develop bleedings in spite of a normal haemostatic mechanism. Achieving satisfactory haemostasis is also a problem when bleedings occur in organs such as the brain, inner ear region and eyes and may also be a problem in cases of diffuse bleedings (haemorrhagic gastritis and profuse uterine bleeding) when it is difficult to identify the source. The same problem may arise in the process of taking biopsies from various organs (liver, lung, tumour tissue, gastrointestinal tract) as well as in laparoscopic surgery. These situations share the difficulty of providing haemostasis by surgical techniques (sutures, clips, etc.). Acute and profuse bleedings may also occur in subjects on anticoagulant therapy in whom a defective haemostasis has been induced by the therapy given. Such subjects may need surgical interventions in case the anticoagulant effect has to be counteracted rapidly. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

A systemic activation of the coagulation cascade may lead to disseminated intravascular coagulation (DIC). However, such complications have not been seen in subjects treated with high doses of recombinant Factor VIIa because of a localised haemostatic process of the kind induced by the complex formation between Factor VIIa and TF exposed at the site of vessel wall injury. The procoagulant Factor VII derivatives according to the invention may thus also be used in their activated form to control such excessive bleedings associated with a normal haemostatic mechanism.

For treatment in connection with deliberate interventions, the procoagulant Factor VII derivatives of the invention will typically be administered within about 24 hours prior to performing the intervention, and for as much as 7 days or more thereafter. Administration as a coagulant can be by a variety of routes as described herein.

The dose of the Factor VII derivatives ranges from about 0.05 mg to 500 mg/day, preferably from about 1 mg to 200 mg/day, and more preferably from about 10 mg to about 175 mg/day for a 70 kg subject as loading and maintenance doses, depending on the severity of the condition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. The compositions for parenteral administration comprise the Factor VII derivative of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The Factor VII derivatives of the invention can also be formulated into liposome preparations for delivery or targeting to the sites of injury. Liposome preparations are generally described in, e.g., U.S. Pat. No. 4,837,028, U.S. Pat. No. 4,501,728, and U.S. Pat. No. 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of Factor VII derivative in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the Factor VII polypeptide. Actual methods for preparing parenterally administrable compositions will be known or apparent to those skilled in the art and are described in more detail in, for example, *Remington's Pharmaceutical Sciences*, 18th ed., Mack Publishing Company, Easton, Pa. (1990).

The compositions containing the Factor VII derivatives of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject. In general, however, the effective amount will range from about 0.05 mg up to about 500 mg of the Factor VII derivative per day for a 70 kg subject, with dosages of from about 1.0 mg to about 200 mg of the Factor VII derivative per day being more commonly used.

It must be kept in mind that the materials of the present invention may generally be employed in serious disease or injury states, that is, life threatening or potentially life threatening situations. In such cases, in view of the minimisation of extraneous substances and general lack of immunogenicity of human Factor VII derivatives in humans, it is possible and may be felt desirable by the treating physician to administer a substantial excess of these variant Factor VII compositions.

In prophylactic applications, compositions containing the Factor VII derivative of the invention are administered to a subject susceptible to or otherwise at risk of a disease state or injury to enhance the subject's own coagulative capability. Such an amount is defined to be a "prophylactically effective dose." In prophylactic applications, the precise amounts once again depend on the subject's state of health and weight, but the dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the Factor VII derivatives may be administered by continuous infusion using e.g. a portable pump system.

Local delivery of the Factor VII derivative of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of Factor VII derivative sufficient to effectively treat the subject.

Inactivated Factor VII polypeptides of the present invention is able to bind to cell-surface tissue factor. For example, DEGR-Factor VIIa binds cell-surface tissue factor with an equivalent or higher affinity than wild-type Factor VIIa. DEGR-Factor VIIa, however, has no enzymatic activity, yet it binds to tissue factor and acts as a competitive antagonist for wild-type Factor VIIa, thereby inhibiting the subsequent steps in the extrinsic pathway of coagulation leading to the generation of thrombin.

Inactivated Factor VII derivatives are particularly useful for administration to humans to treat a variety of conditions involving intravascular coagulation. For example, although deep vein thrombosis and pulmonary embolism can be treated with conventional anticoagulants, the inactivated Factor VII derivatives described herein may be used to prevent the occurrence of thromboembolic complications in identified high risk patients, such as those undergoing surgery or those with congestive heart failure. In addition, inactivated Factor VII derivatives may act as an antagonist for tissue factor-mediated induction of coagulation, thus blocking the production of thrombin and the subsequent deposition of fibrin. As such, inactivated Factor VII derivatives may be useful for inhibiting tissue factor activity resulting in, for example, the inhibition of blood coagulation, thrombosis or platelet deposition.

The inactivated Factor VII derivatives may be particularly useful in the treatment of intimal hyperplasia, restenosis due to acute vascular injury, deep venous thrombosis, arterial thrombosis, post surgical thrombosis, coronary artery bypass graft (CABG), percutaneous transdermal coronary angioplasty (PTCA), stroke, cancer, tumour metastasis, angiogenesis, ischemia/reperfusion, rheumatoid arthritis, thrombolysis, arteriosclerosis and restenosis following angioplastry, acute and chronic indications such as inflammation, septic chock, septicemia, hypotension, adult respiratory distress syndrome (ARDS), disseminated intravascular coagulopathy (DIC), pulmonary embolism, platelet deposition, myocardial infarction, or the prophylactic treatment of mammals with atherosclerotic vessels at risk for thrombosis. Acute vascular injuries are those which occur rapidly (i.e. over days to months), in contrast to chronic vascular injuries (e.g. atherosclerosis) which develop over a lifetime. Acute vascular injuries often result from surgical procedures such as vascular reconstruction, wherein the techniques of angioplasty, endarterectomy, atherectomy, vascular graft emplacement or the like are employed. Hyperplasia may also occur as a delayed response in response to, e.g., graft emplacement or organ transplantation. Since inactivated Factor VII derivatives is more selective than heparin, generally binding only tissue factor which has been exposed at sites of injury, and because inactivated Factor VII derivatives does not destroy other coagulation proteins, it will be more effective and less likely to cause bleeding complications than heparin when used prophylactically for the prevention of deep vein thrombosis.

Inactivated Factor VII derivatives which maintain tissue factor binding inhibit platelet accumulation at the site of vascular injury by blocking the production of thrombin and the subsequent deposition of fibrin.

Due to the ability of DEGR-Factor VII to block thrombin generation and limit platelet deposition at sites of acute vascular injury, inactivated Factor VII derivatives which maintain tissue factor binding activity but lack Factor VIIa enzymatic activity can be used to inhibit vascular restenosis.

Compositions comprising inactivated Factor VII derivatives are particularly useful in methods for treating patients when formulated into pharmaceutical compositions, where they may be given to individuals suffering from a variety of disease states to treat coagulation-related conditions. Such inactivated Factor VII derivatives, capable of binding tissue factor but having a substantially reduced ability to catalyze activation of other factors in the clotting cascade, may possess a longer plasma half-life and thus a correspondingly longer period of anticoagulative activity when compared to other anticoagulants. Among the medical indications for the subject compositions are those commonly treated with anticoagulants, such as, for example, deep vein thrombosis, pulmonary embolism, stroke, disseminated intravascular coagulation (DIC), fibrin deposition in lungs and kidneys associated with gram-negative endotoxemia, and myocardial infarction. The compositions can be used to inhibit vascular restenosis as occurs following mechanical vascular injury, such as injury caused by balloon angioplasty, endarterectomy, reductive atherectomy, stent placement, laser therapy or rotablation, or as occurs secondary to vascular grafts, stents, bypass grafts or organ transplants. The compositions can thus be used to inhibit platelet deposition and associated disorders. Thus, a method of inhibiting coagulation, vascular restenosis or platelet deposition, for example, comprises administering to a patient a composition comprising inactivated Factor VII derivatives, such as that having at least one amino acid substitution in a catalytic triad of Ser344, Asp242 and Hisl93, in an amount sufficient to effectively inhibit coagulation, vascular restenosis or platelet deposition. The methods also find use in the treatment of acute closure of a coronary artery in an individual (e.g. acute myocardial infarction), which comprises administering the inactivated Factor VII derivatives, which includes DEGR-Factor VII and FFR-Factor VII, in conjunction with tissue plasminogen activator or streptokinase, and can accelerate tPA induced thrombolysis. The inactivated Factor VII derivatives is given prior to, in conjunction with, or shortly following administration of a thrombolytic agent, such as tissue plasminogen activator.

Compositions of inactivated Factor VII derivatives will also have substantial utility in the prevention of cardiogenic emboli and in the treatment of thrombotic strokes. Because of its low potential for causing bleeding complications and its selectivity, Factor VII derivatives can be given to stroke victims and may prevent the extension of the occluding arterial thrombus. The amount of Factor VII derivatives administered will vary with each patient depending on the nature and severity of the stroke, but doses will generally be in the range of those suggested below.

Inactivated Factor VII derivatives and compositions thereof can also be used to inhibit deleterious events associated with ischemic reperfusion. Severe ischemia to a tissue, organ or limb may be due to a decrease in blood flow and may be associated with trauma, surgical manipulation, or lowered blood pressure. One of the complications associated with severe ischemia is the up-regulation of tissue factor in the arterial system. This increased expression of tissue factor is believed to stimulate a procoagulant response, primarily in the capillary bed. Following reperfusion to the ischemic tissue, thrombi can be generated which may be either occlusive or non-occlusive. The generation of thrombi in the arterial bed, and the deposition of platelets along the thrombus, lead to the secondary generation of ischemia to the tissue. The generation of the thrombi and the presence of platelets can then cause the generation and release of multiple bioactive factors, including those generated from the coagulation pathway, such as thrombin and Factor X, as well as factors released from activated platelets. In turn, these factors may induce the generation of additional factors by the underlying endothelial and smooth muscle cells, or by adjacent mononuclear cells, such as TNF-alpha and IL-1. These factors, in turn, can then activate the endothelial cells leading to the up-regulation of various adhesion molecules associated with monocyte and neutrophil binding. The binding and transmigration of monocytes and neutrophils, the release of bioactive compounds by these cells, including the generation of free-oxygen radicals, can exacerbate the level of endothelial cell activation and damage. Ultimately, if the cascade of events goes unchecked, this can lead to systemic complications and the potential to stimulate multiple organ failure. By blocking tissue factor according to the present invention by administering a specific inhibitor for tissue factor/Factor VII binding (e.g., FFR-FVIIa), and thereby blocking the initiation of the extrinsic pathway of coagulation, the initiation of the cascade of events may be prevented, thereby eliminating, or minimizing the deleterious events associated with ischemia/reperfusion.

The dose of inactivated Factor VII derivatives for prevention of deep vein thrombosis is in the range of about 50 µg to 500 mg/day, more typically 1 mg to 200 mg/day, and more preferably 10 to about 175 mg/day for a 70 kg patient, and administration should begin at least about 6 hours prior to surgery and continue at least until the patient becomes ambulatory. The dose of inactivated Factor VII derivatives in the treatment for restenosis will vary with each patient but will generally be in the range of those suggested above.

Compositions comprising inactivated Factor VII derivatives will typically be administered within about 24 hours prior to performing an intervention, and for as much as 7 days or more thereafter. Administration can be by a variety of routes as further described herein. The compositions comprising inactivated Factor VII derivatives can also be administered systemically or locally for the placement of vascular grafts (e.g., by coating synthetic or modified natural arterial vascular grafts), at sites of anastomosis, surgical endarterectomy (typically carotid artery endarterectomy), bypass grafts, and the like.

In the treatment of established deep vein thrombosis and/or pulmonary embolism, the dose of Factor VII derivatives ranges from about 50 µg to 500 mg/day, more typically 1 mg to 200 mg/day, and more preferably 10 mg to about 175 mg/day for a 70 kg patient as loading and maintenance doses, depending on the weight of the patient and the severity of the condition. Because of the lower likelihood of bleeding complications from infusions of inactivated Factor VII derivatives, inactivated Factor VII derivatives can replace or lower the dose of heparin during or after surgery in conjunction with thrombectomies or embolectomies.

In cases of acute bacteremia, endotoxemia or DIC, the patient is given a loading dose of a Factor VII derivative of at least about 50 µg to 500 mg/day, more typically 1 mg to 200 mg/day, and more preferably 10 mg to about 175 mg/day for a 70 kg patient, with maintenance doses thereafter in the range of 50 µg to 500 mg/day, typically 1 mg to 200 mg/day for a 70 kg patient.

Preferably, the Factor VII derivative has a half-life ($t_{1/2}$) which is enhanced relative to the half-life of the unconjugated Factor VII from which it was derived. Preferably, the half-life of the Factor VII derivative is enhanced by at least 1.5-fold to 2-fold, more preferably by about 2-fold to 3-fold, even more preferably by about 5-fold to 10-fold, optimally about 100-fold, usually about 6-fold relative to the half-life of the unmodified parent Factor VII.

General methods of attaching polyethylene glycol to proteins are disclosed within U.S. Pat. No. 4,179,337 issued Dec. 18, 1979 (incorporated herein by reference to disclose methods of attaching polyethylene glycol to proteins). Further, other methods of attaching polyethylene glycol are disclosed within U.S. Pat. No. 5,122,614 issued Jun. 16, 1992, also incorporated herein by reference to disclose methods of attaching polyethylene glycol to proteins. Maleimido-PEG is perhaps the most useful reagent for cysteine-PEGylation, but other chemistries are available for specific cysteine modification.

BRIEF DESCRIPTION OF THE DRAWINGS

The present invention is described in further detail in the examples with reference to the appended drawings wherein FIG. 1 The structure of correctly processed human coagulation Factor VII, amino acids 1 to 406 SEQ ID NO: 1, with gamma carboxylated Glu-residues (γ) and glycosylation (*). The arrow at amino acid residue 152 shows the site where single-chain Factor VII is cleaved to be converted to activated two-chain Factor VII (FVIIa).

Figure 1:
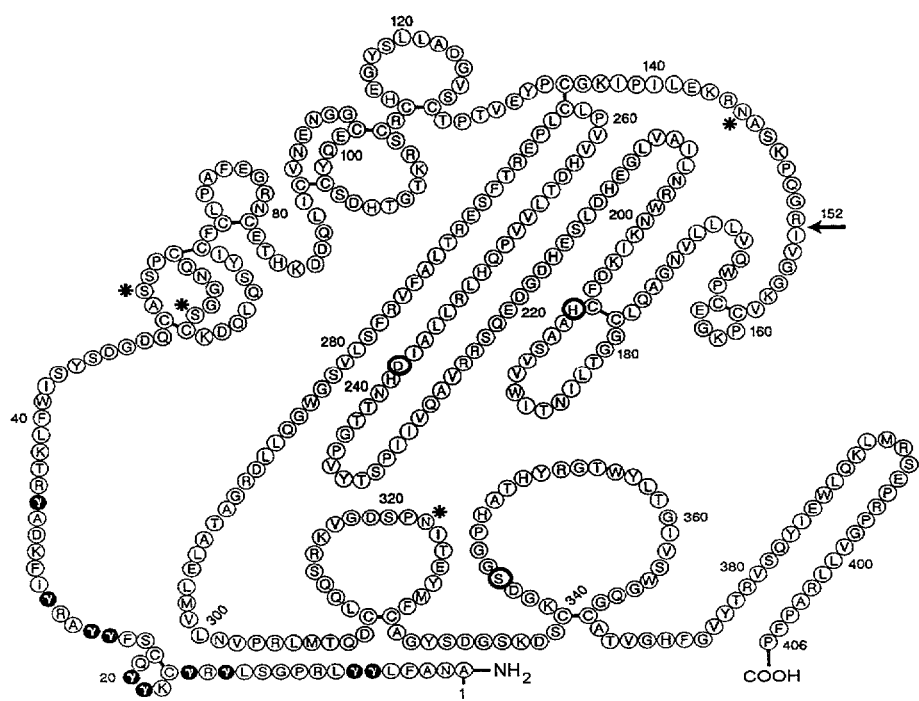
Figure 2:
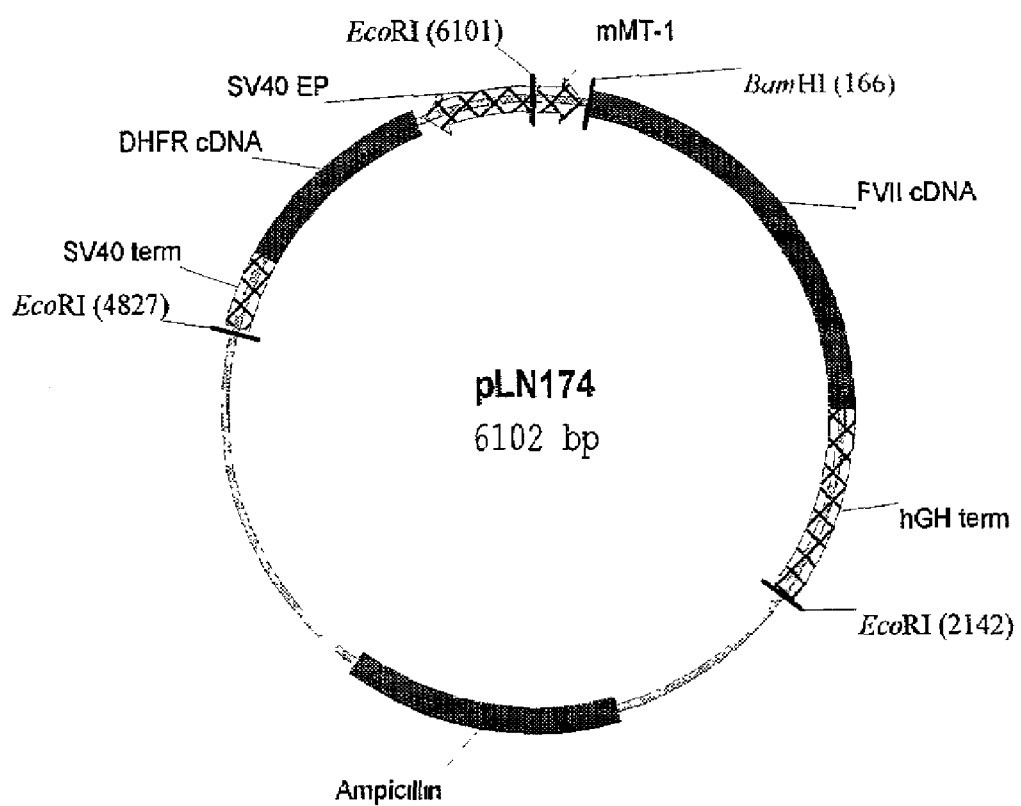
FIG. 2 Construction of plasmids for expression of recombinant human Factor VII polypeptides. Plasmid pLN174 express human Factor VII with connected propeptide naturally associated with Factor VII.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

The terminology for amino acid substitutions used the following examples are as follows. The first letter represent the amino acid naturally present at a position of SEQ ID NO: 1. The following number represent the position in SEQ ID NO: 1. The second letter represent the different amino acid substituting for the natural amino acid. An example is R396C, where an arginine at position 396 of SEQ ID NO: 1 is replaced by a cysteine. In another example, V158T/M298Q, the valine in position 158 of SEQ ID NO: 1 is replaced by a threonine and the methionine in position 298 of SEQ ID NO: 1 is replaced by a Glutamine in the same Factor VII polypeptide.

Example 1

Construction of DNA Encoding FVII-(R396C), FVII-(Q250C), FVII-(P406C), FVII-(407C), FVII-(V158T/M298Q), FVII-(L305V/M306D/D309S), FVII-(K337A), FVII-(L305V), and FVII-(F374P):

DNA constructs encoding FVII-(R396C), FVII-(Q250C), FVII-(P406C), FVII-(407C) (One additional C-terminal Cys), FVII-(M298Q), FVII-(L305V/M306D/D309S), FVII-(K337A), FVII-(L305V), and FVII-(F374P) was prepared by site-directed mutagenesis using a supercoiled, double stranded DNA vector with insert of human FVII (pLN174) and two synthetic primers containing the desired mutation. The following primers were used:

```
For FVII-(R396C):
5'-GCG CTC AGA GCC ATG CCC AGG AGT CCT CC-3'        (SEQ ID NO: 3)
5'-GGA GGA CTC CTG GGC ATG GCT CTG AGC GC-3'        (SEQ ID NO: 4)

For FVII-(Q250C):
5'-GCT CCG CCT GCA CTG TCC CGT GGT CCT CAC TGA CC-3'  (SEQ ID NO: 5)
5'-GGT CAG TGA GGA CCA CGG GAC AGT GCA GGC GGA GC-3'  (SEQ ID NO: 6)

For FVII-(P406C):
5'-GCG AGC CCC ATT TGC TA GAC TAG AGG ATC TGG G-3'    (SEQ ID NO: 7)
5'-CCC AGA TCC TCT AGT CTA GCA AAA TGG GGC TCG C-3'   (SEQ ID NO: 8)

For FVII-(407C):
5'-CCT GCG AGC CCC ATT TCC CTC TTA GAC TAG AGG ATC TGG G-3'  (SEQ ID NO: 9)
5'-CCC AGA TCC TCT AGT CTA ACA GGG AAA TGG GGC TCG CAG G-3'  (SEQ ID NO: 10)

For FVII-(M298Q):
5'-GCC CTG GAG CTC CAG GTC CTC AAC GTG CCC-3'       (SEQ ID NO: 11)
5'-GGG CAC GTT GAG GAC CTG GAG CTC CAG GGC-3'       (SEQ ID NO: 12)

For FVII-(L305V):
5'-CGT GCC CCG GGT GAT GAC CCA GGA C-3'              (SEQ ID NO: 13)
5'-GTC CTG GGT CAT CAC CCG GGG CAC G-3'              (SEQ ID NO: 14)

For FVII-(M306D/D309S):
5'-TCT AGA TAC CCA GTC TTG CCT GCA GCA GTC ACG GAA-3'  (SEQ ID NO: 15)
5'-TTC CGT GAC TGC TGC AGG CAA GAC TGG GTA TCT AGA-3'  (SEQ ID NO: 16)

For FVII-(K337A):
5'-CGG ATG GCA GCG CGG ACT CCT GCA AGG G-3'          (SEQ ID NO: 17)
5'-CCC TTG CAG GAG TCC GCG CTG CCA TCC G-3'          (SEQ ID NO: 18)

For FVII-(F374P):
5'-CCG TGG GCC ACC CTG GGT GTA CAC C-3'              (SEQ ID NO: 19)
5'-GGT GTA CAC CCA GGG TGG CCC ACG G-3'              (SEQ ID NO: 20)
```

The oligonucleotide primers, each complementary to opposite strands of the vector insert, were extended during temperature cycling by means of Pfu DNA polymerase. On incorporation of the primers, a mutated plasmid containing staggered nicks was generated. Following temperature cycling, the product was treated with DpnI which is specific for methylated and hemimethylated DNA to digest the parental DNA template and to select for mutation-containing synthesized DNA.

Procedures for preparing a DNA construct using polymerase chain reaction using specific primers are well known to persons skilled in the art (cf. *PCR Protocols*, 1990, Academic ress, San Diego, Calif., USA).

Example 2

Preparation of FVII-(R396C).

BHK cells were transfected essentially as previously described (Thim et al. (1988) *Biochemistry* 27, 7785–7793; Persson and Nielsen (1996) *FEBS Lett.* 385, 241–243) to obtain expression of the variant FVII-(R396C). The Factor VII polypeptide was purified as follows:

Conditioned medium was loaded onto a 25-ml column of Q Sepharose Fast Flow (Pharmacia Biotech) after addition of 5 mM EDTA, 0.1% Triton X-100 and 10 mM Tris, adjustment of pH to 8.0 and adjustment of the conductivity to 10–11 mS/cm by adding water. Elution of the protein was accomplished by a gradient from 10 mM Tris, 50 mM NaCl, 0.1% Triton X-100, pH 8.0 to 10 mM Tris, 50 mM NaCl, 25 mM $CaCl_2$, 0.1% Triton X-100, pH 7.5. The fractions containing FVII-(R396C) were pooled, and applied to a 25-ml column containing the monoclonal antibody F1A2 (Novo Nordisk, Bagsvaerd, Denmark) coupled to CNBr-activated Sepharose 4B (Pharmacia Biotech). The column was equilibrated with 50 mM Hepes, pH 7.5, containing 10 mM $CaCl_2$, 100 mM NaCl and 0.02% Triton X-100. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or FVII-(R396C) was transferred to a $Ca^{2+}$-containing buffer. The yield of each step was followed by factor VII ELISA measurements and the purified protein was analysed by SDS-PAGE.

Example 3

Preparation of FVII-(M298Q).

BHK cells were transfected essentially as previously described (Thim et al. (1988) *Biochemistry* 27, 7785–7793; Persson and Nielsen (1996) *FEBS Lett.* 385, 241–243) to obtain expression of the variant FVII-(V158T/M2980). The Factor VII polypeptide was purified as follows:

Conditioned medium was loaded onto a 25-ml column of Q Sepharose Fast Flow (Pharmacia Biotech) after addition of 5 mM EDTA, 0.1% Triton X-100 and 10 mM Tris, adjustment of pH to 8.0 and adjustment of the conductivity to 10–11 mS/cm by adding water. Elution of the protein was accomplished by a gradient from 10 mM Tris, 50 mM NaCl, 0.1% Triton X-100, pH 8.0 to 10 mM Tris, 1 M NaCl, 5 mM $CaCl_2$, 0.1% Triton X-100, pH 7.5. The fractions containing FVII-(V158T/M298Q) were pooled, 10 mM $CaCl_2$ was added, and applied to a 25-ml column containing monoclonal antibody F1A2 (Novo Nordisk, Bagsvaerd, Denmark) coupled to CNBr-activated Sepharose 4B (Pharmacia Biotech). The column was equilibrated with 50 mM Hepes, pH 7.5, containing 10 mM $CaCl_2$, 100 mM NaCl and 0.02% Triton X-100. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or FVII-(V158T/M298Q) was transferred to a $Ca^{2+}$-containing buffer. The yield of each step was followed by factor VII ELISA measurements and the purified protein was analysed by SDS-PAGE.

Example 4

Preparation of FVII-(L305V/M306D/D309S).

BHK cells were transfected essentially as previously described (Thim et al. (1988) *Biochemistry* 27, 7785–7793; Persson and Nielsen (1996) *FEBS Lett.* 385, 241–243) to obtain expression of the variant FVII-(L305V/M306D/D309S). The Factor VII polypeptide was purified as follows:

Conditioned medium was loaded onto a 25-ml column of Q Sepharose Fast Flow (Pharmacia Biotech) after addition of 5 mM EDTA, 0.1% Triton X-100 and 10 mM Tris, adjustment of pH to 8.0 and adjustment of the conductivity to 10–11 mS/cm by adding water. Elution of the protein was accomplished by a gradient from 10 mM Tris, 50 mM NaCl, 0.1% Triton X-100, pH 8.0 to 10 mM Tris, 1 M NaCl, 5 mM $CaCl_2$, 0.1% Triton X-100, pH 7.5. The fractions containing FVII-(L305V/M306D/D309S) were pooled, 10 mM $CaCl_2$ was added, and applied to a 25-ml column containing monoclonal antibody F1A2 (Novo Nordisk, Bagsvaerd, Denmark) coupled to CNBr-activated Sepharose 4B (Pharmacia Biotech). The column was equilibrated with 50 mM Hepes, pH 7.5, containing 10 mM $CaCl_2$, 100 mM NaCl and 0.02% Triton X-100. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or FVII-(L305V/M306D/D309S) was transferred to a $Ca^{2+}$-containing buffer. The yield of each step was followed by factor VII ELISA measurements and the purified protein was analysed by SDS-PAGE.

Example 5

In Vitro Hydrolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=($A_{405\ nm}$ Factor VIIa variant)/($A_{405\ nm}$ Factor VIIa wild-type).

Example 6

In Vitro Proteolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A_{405\ nm}$ Factor VIIa variant)/($A_{405\ nm}$ Factor VIIa wild-type).

Example 7

Relative Activities of FVIIa Polypeptides Measured in the Assays Described in Examples 5 and 6

| Variant | Ratio in example 5 | Ratio in example 6 |
| --- | --- | --- |
| FVIIa-(M298Q) | 3.5 ± 0.2 | 12 ± 1 |
| FVIIa-(V158D/E296V/M298Q) | 7.5 ± 0.4 | 38 ± 5 |
| FVIIa-(K337A) | 4.0 ± 0.2 | 4.1 ± 0.4 |
| FVIIa-(L305V/M306D/D309S) | 3.0 ± 0.1 | 3.7 ± 0.3 |
| FVIIa-(L305V) | 3.2 ± 0.2 | 3.3 ± 0.2 |
| FVIIa-(F374P) | 1.4 | <1 |
| FVIIa-(R396C) | 1.0 | 1.0 |
| FVIIa-(Q250C) | 1.0 | 1.5 |
| FVIIa-(P406C) | 0.8 | 1.0 |
| FVIIa-(407C) | 1.1 | 1.4 |
| wt-FVIIa | 1.0 | 1.0 |

Example 8

PEG Conjugation of FVII-(R396C), FVII-(Q250C), FVII-(P406C), FVII-(407C)

The Factor VIIa variants as described in example 1, with a free thiol group introduced at any of the mentioned positions (250, 396, 406 or 407 (the latter C-terminally extended)) are reacted with a 5-fold molar excess of PEG vinylsulfone or PEG-maleimide (alternatively any other sulfhydryl-reactive PEG derivative may be used) in an aqueous buffer for 3 hours to drive the reaction virtually to completion. The molecular weight of the PEG derivative is at least 10,000. The resulting PEG-FVIIa are tested for amidolytic and proteolytic activity as described in examples 5 and 6 and should retain the activity of wild-type human FVIIa, or if a Cys has been introduced into a FVIIa variant with increased activity, the activity after reaction with the PEG derivative should remain higher than that of wild-type human FVIIa. PEG-conjugated FVIIa is separated from unreacted FVIIa variant and free PEG derivative by means of chromatography such as gel filtration on a column of Superdex-200 or the like.

PEG Conjugation of proteins at Cys residues is known to the person skilled in the art and described in several publication including Goodson, R. J. & Katre, N. V. (1990) Bio/Technology 8, 343 and Kogan, T. P. (1992) Synthetic Comm. 22, 2417.

What is claimed is:

1. A human Factor VII variant polypeptide, said polypeptide comprising the amino acid sequence of SEQ ID NO: 1 in which at least one amino acid has been substituted with a different amino acid or inserted, wherein said variant comprises a substitution or insertion selected from the group consisting of: Q250C; P406C; and 407C.

2. The polypeptide as defined in claim 1, wherein the different substituted or inserted amino acid is conjugated with a chemical group that increases the actual molecular weight of the conjugated polypeptide relative to the molecular weight of the variant polypeptide when unconjugated from about 300 daltons to about 100,000 daltons and wherein said conjugated polypeptide has substantially the same activity or increased activity compared to recombinant wild type human Factor VIIa.

3. The polypeptide as defined in claim 2, wherein said chemical group is substantially neutral.

4. The polypeptide as defined in claim 2, wherein said increase in molecular weight is from about 1,000 daltons to about 80,000 daltons.

5. The polypeptide as defined in claim 4, wherein said increase in molecular weight is from about 5,000 daltons to about 60,000 daltons.

6. The polypeptide as defined in claim 5, wherein said increase in molecular weight is from about 10,000 daltons to about 40,000 daltons.

7. The polypeptide as defined in claim 2, wherein said chemical group is polyethylene glycol.

8. A pharmaceutical composition comprising the Factor VII variant polypeptide as defined in claim 1 and, optionally, a pharmaceutically acceptable carrier.

9. A method for the treatment of bleeding episodes or bleeding disorders in a subject or for the enhancement of the normal haemostatic system, said method comprising administering to a subject in need thereof a therapeutically or prophylactically effective amount of the Factor VII variant polypeptide as defined in claim 2.

* * * * *

SEQUENCE LISTING

```
<160> NUMBER OF SEQ ID NOS: 20

<210> SEQ ID NO 1
<211> LENGTH: 406
<212> TYPE: PRT
<213> ORGANISM: Homo sapiens
<220> FEATURE:
<221> NAME/KEY: VARIANT
<222> LOCATION: (1)...(406)
<223> OTHER INFORMATION: Xaa = Any Amino Acid

<400> SEQUENCE: 1

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
            35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110
```

Arg Cys His Glu Gly Tyr Ser Leu Leu Ala Asp Gly Val Ser Cys Thr
    115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Lys Val Cys Pro
145                 150                 155                 160

Lys Gly Glu Cys Pro Trp Gln Val Leu Leu Val Asn Gly Ala Gln
                165                 170                 175

Leu Cys Gly Gly Thr Leu Ile Asn Thr Ile Trp Val Val Ser Ala Ala
                180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
                260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 2
<211> LENGTH: 6098
<212> TYPE: DNA
<213> ORGANISM: Artificial Sequence
<220> FEATURE:
<223> OTHER INFORMATION: Plasmid DNA plN174

<400> SEQUENCE: 2
ttcgagctct gcactccgcc cgaaaagtgc gctcggctct gccaaggacg cggggcgcgt      60
gactatgcgt gggctggagc aaccgcctgc tgggtgcaaa ccctttgcgc ccggactcgt     120
ccaacgacta taagagggc aggctgtcct ctaagcgtca cccgggatcc atggtctccc     180
aggccctcag gctcctctgc cttctgcttg ggcttcaggg ctgcctggct gcagtcttcg     240
taacccagga ggaagcccaa ggcgtcctgc accggcgccg gcgcgccaac gcgttcctgg     300
aggagctgcg gccgggctcc ctggagaggg agtgcaagga ggagcagtgc tccttcgagg     360

-continued

| | |
|---|---|
| aggcccggga gatcttcaag gacgcggaga ggacgaagct gttctggatt tcttacagtg | 420 |
| atggggacca gtgtgcctca agtccatgcc agaatggggg ctcctgcaag gaccagctcc | 480 |
| agtcctatat ctgcttctgc ctccctgcct tcgagggccg gaactgtgag acgcacaagg | 540 |
| atgaccagct gatctgtgtg aacgagaacg gcggctgtga gcagtactgc agtgaccaca | 600 |
| cgggcaccaa gcgctcctgt cggtgccacg aggggtactc tctgctggca gacggggtgt | 660 |
| cctgcacacc cacagttgaa tatccatgtg gaaaaatacc tattctagaa aaagaaatg | 720 |
| ccagcaaacc ccaaggccga attgtggggg gcaaggtgtg ccccaaaggg gagtgtccat | 780 |
| ggcaggtcct gttgttggtg aatggagctc agttgtgtgg ggggaccctg atcaacacca | 840 |
| tctgggtggt ctccgcggcc cactgtttcg acaaaatcaa gaactggagg aacctgatcg | 900 |
| cggtgctggg cgagcacgac ctcagcgagc acgacgggga tgagcagagc cggcgggtgg | 960 |
| cgcaggtcat catccccagc acgtacgtcc cgggcaccac caaccacgac atcgcgctgc | 1020 |
| tccgcctgca ccagcccgtg gtcctcactg accatgtggt gccctctgc ctgcccgaac | 1080 |
| ggacgttctc tgagaggacg ctggccttcg tgcgcttctc attggtcagc ggctggggcc | 1140 |
| agctgctgga ccgtggcgcc acggccctgg agctcatggt cctcaacgtg ccccggctga | 1200 |
| tgacccagga ctgcctgcag cagtcacgga aggtgggaga ctccccaaat atcacggagt | 1260 |
| acatgttctg tgccggctac tcggatggca gcaaggactc ctgcaagggg gacagtggag | 1320 |
| gcccacatgc cacccactac cggggcacgt ggtacctgac gggcatcgtc agctggggcc | 1380 |
| agggctgcgc aaccgtgggc cactttgggg tgtacaccag ggtctcccag tacatcgagt | 1440 |
| ggctgcaaaa gctcatgcgc tcagagccac gcccaggagt cctcctgcga gcccatttc | 1500 |
| cctagactag aggatctggg gtggcatccc tgtgacccct ccccagtgcc tctcctggcc | 1560 |
| ctggaagttg ccactccagt gcccaccagc cttgtcctaa taaaattaag ttgcatcatt | 1620 |
| ttgtctgact agtgtccctt ctataatatt atgggtgga gggggtggt atggagcaag | 1680 |
| gggcaagttg ggaagacaac ctgtagggcc tgcgggtct attgggaacc aagctggagt | 1740 |
| gcagtggcac aatcttggct cactgcaatc tccgcctcct gggttcaagc gattctcctg | 1800 |
| cctcagcctc ccgagttgtt gggattccag gcatgcatga ccaggctcag ctaatttttg | 1860 |
| tttttttggt agagacgggg tttcaccata ttggccaggc tggtctccaa ctcctaatct | 1920 |
| caggtgatct acccaccttg gcctcccaaa ttgctgggat tacaggcgtg aaccactgct | 1980 |
| cccttccctg tccttctgat tttaaaataa ctataccagc aggaggacgt ccagacacag | 2040 |
| cataggctac ctggccatgc ccaaccggtg ggacatttga gttgcttgct tggcactgtc | 2100 |
| ctctcatgcg ttgggtccac tcagtagatg cctgttgaat tcgagctcgc ccgggctcta | 2160 |
| gctagagtcg acctgcaggc atgcaagctt tggcactggc cgtcgtttta caacgtcgtg | 2220 |
| actgggaaaa ccctggcgtt acccaactta atcgccttgc agcacatccc cctttcgcca | 2280 |
| gctggcgtaa tagcgaagag gcccgcaccg atcgcccttc ccaacagttg cgcagcctga | 2340 |
| atggcgaatg cgcctgatg cggtattttc ttccttacgc atctgtgcgg tatttcacac | 2400 |
| cgcatatggt gcactctcag tacaatctgc tctgatgccg catagttaag ccagccccga | 2460 |
| cacccgccaa cacccgctga cgcgccctga cgggcttgtc tgctcccggc atccgcttac | 2520 |
| agacaagctg tgaccgtctc cgggagctgc atgtgtcaga ggttttcacc gtcatcaccg | 2580 |
| aaacgcgcga gacgaaaggg cctcgtgata cgcctatttt tataggttaa tgtcatgata | 2640 |
| ataatggttt cttagacgtc aggtggcact tttcggggaa atgtgcgcgg aaccccctatt | 2700 |
| tgtttatttt tctaaataca ttcaaatatg tatccgctca tgagacaata accctgataa | 2760 |

```
atgcttcaat aatattgaaa aaggaagagt atgagtattc aacatttccg tgtcgccctt      2820
attccctttt ttgcggcatt tgccttcct gttttgctc acccagaaac gctggtgaaa       2880
gtaaaagatg ctgaagatca gttgggtgca cgagtgggtt acatcgaact ggatctcaac      2940
agcggtaaga tccttgagag ttttcgcccc gaagaacgtt ttccaatgat gagcactttt      3000
aaagttctgc tatgtggcgc ggtattatcc cgtattgacg ccgggcaaga gcaactcggt      3060
cgccgcatac actattctca gaatgacttg gttgagtact caccagtcac agaaaagcat      3120
cttacggatg gcatgacagt aagagaatta tgcagtgctg ccataaccat gagtgataac      3180
actgcggcca acttacttct gacaacgatc ggaggaccga aggagctaac cgctttttg       3240 cacaacatgg gggatcatgt aactcgcctt gatcggttgg gaaccggagc tgaatgaagc      3300
cataccaaac gacgagcgtg acaccacgat gcctgtagca atggcaacaa cgttgcgcaa      3360
actattaact ggcgaactac ttactctagc ttcccggcaa caattaatag actggatgga      3420
ggcggataaa gttgcaggac cacttctgcg ctcggccctt ccggctggct ggtttattgc      3480
tgataaatct ggagccggtg agcgtgggtc tcgcggtatc attgcagcac tggggccaga      3540
tggtaagccc tcccgtatcg tagttatcta cacgacgggg agtcaggcaa ctatggatga      3600
acgaaataga cagatcgctg agataggtgc ctcactgatt aagcattggt aactgtcaga      3660
ccaagtttac tcatatatac tttagattga tttaaaactt catttttaat ttaaaaggat      3720
ctaggtgaag atcctttttg ataatctcat gaccaaaatc ccttaacgtg agttttcgtt      3780
ccactgagcg tcagacccg tagaaaagat caaaggatct tcttgagatc cttttttct       3840 gcgcgtaatc tgctgcttgc aaacaaaaaa ccaccgctac cagcggtggt ttgtttgccg      3900
gatcaagagc taccaactct ttttccgaag gtaactggct tcagcagagc gcagatacca      3960
aatactgtcc ttctagtgta gccgtagtta ggccaccact tcaagaactc tgtagcaccg      4020
cctacatacc tcgctctgct aatcctgtta ccagtggctg ctgccagtgg cgataagtcg      4080
tgtcttaccg ggttggactc aagacgatag ttaccggata aggcgcagcg gtcgggctga      4140
acggggggtt cgtgcacaca gcccagcttg gagcgaacga cctacaccga actgagatac      4200
ctacagcgtg agctatgaga aagcgccacg cttcccgaag ggagaaaggc ggacaggtat      4260
ccggtaagcg gcagggtcgg aacaggagag cgcacgaggg agcttccagg gggaaacgcc      4320
tggtatcttt atagtcctgt cgggtttcgc cacctctgac ttgagcgtcg attttgtga      4380 tgctcgtcag ggggcggag cctatggaaa aacgccagca acgcggcctt tttacggttc       4440
ctggcctttt gctggccttt tgctcacatg ttctttcctg cgttatcccc tgattctgtg      4500
gataaccgta ttaccgcctt tgagtgagct gataccgctc gccgcagccg aacgaccgag      4560
cgcagcgagt cagtgagcga ggaagcggaa gagcgcccaa tacgcaaacc gcctctcccc      4620
gcgcgttggc cgattcatta atgcagctgg cacgacaggt ttcccgactg gaaagcgggc      4680
agtgagcgca acgcaattaa tgtgagttag ctcactcatt aggcaccca ggctttacac       4740 tttatgcttc cggctcgtat gttgtgtgga attgtgagcg gataacaatt tcacacagga      4800
aacagctatg accatgatta cgaattcatc gatatctaga tccagacatg ataagataca      4860
ttgatgagtt tggacaaacc acaactagaa tgcagtgaaa aaaatgcttt atttgtgaaa      4920
tttgtgatgc tattgcttta tttgtaacca ttataagctg caataaacaa gttaacaaca      4980
acaattgcat tcattttatg tttcaggttc agggggaggt gtgggaggtt ttttaaagca      5040
agtaaaacct ctacaaatgt ggtatggctg attatgatct aaagccagca aaagtcccat      5100
```

```
ggtcttataa aaatgcatag ctttaggagg ggagcagaga acttgaaagc atcttcctgt      5160
tagtctttct tctcgtagac ttcaaactta tacttgatgc cttttcctc ctggacctca       5220 gagaggacgc ctgggtattc tgggagaagt ttatatttcc ccaaatcaat ttctgggaaa      5280
aacgtgtcac tttcaaattc ctgcatgatc cttgtcacaa agagtctgag gtggcctggt      5340
tgattcatgg cttcctggta aacagaactg cctccgacta tccaaaccat gtctacttta      5400
cttgccaatt ccggttgttc aataagtctt aaggcatcat ccaaactttt ggcaagaaaa      5460
tgagctcctc gtggtggttc tttgagttct ctactgagaa ctatattaat tctgtccttt      5520
aaaggtcgat tcttctcagg aatggagaac caggttttcc tacccataat caccagattc      5580 tgtttaccttt ccactgaaga ggttgtggtc attctttgga agtacttgaa ctcgttcctg     5640
agcggaggcc agggtaggtc tccgttcttg ccaatcccca tattttggga cacggcgacg      5700
atgcagttca atggtcgaac catgatggca cggatctcga gctcgcgaaa gcttttttgca    5760 aaagcctagg cctccaaaaa agcctcctca ctacttctgg aatagctcag aggccgaggc     5820
ggcctcggcc tctgcataaa taaaaaaaat tagtcagcca tggggcggag aatgggcgga    5880
actgggcgga gttaggggcg ggatgggcgg agttaggggc gggactatgg ttgctgacta     5940
attgagatgc atgctttgca tacttctgcc tgctggggag cctggggact ttccacacct     6000
ggttgctgac taattgagat gcatgctttg catacttctg cctgctgggg agcctgggga    6060 cttttccacac cctaactgac acacattcca caggggaa                            6098
```

<210> SEQ ID NO 3
<211> LENGTH: 29
<212> TYPE: DNA
<213> ORGANISM: Artificial Sequence
<220> FEATURE:
<223> OTHER INFORMATION: Nucleotide Primer

<400> SEQUENCE: 3
gcgctcagag ccatgcccag gagtcctcc                                          29

<210> SEQ ID NO 4
<211> LENGTH: 29
<212> TYPE: DNA
<213> ORGANISM: Artificial Sequence
<220> FEATURE:
<223> OTHER INFORMATION: Nucleotide Primer

<400> SEQUENCE: 4
ggaggactcc tgggcatggc tctgagcgc                                          29

<210> SEQ ID NO 5
<211> LENGTH: 35
<212> TYPE: DNA
<213> ORGANISM: Artificial Sequence
<220> FEATURE:
<223> OTHER INFORMATION: Nucleotide Primer

<400> SEQUENCE: 5
gctccgcctg cactgtcccg tggtcctcac tgacc                                   35

<210> SEQ ID NO 6
<211> LENGTH: 35
<212> TYPE: DNA
<213> ORGANISM: Artificial Sequence
<220> FEATURE:
<223> OTHER INFORMATION: Nucleotide Primer

<400> SEQUENCE: 6
ggtcagtgag gaccacggga cagtgcaggc ggagc                                35

<210> SEQ ID NO 7
<211> LENGTH: 34
<212> TYPE: DNA
<213> ORGANISM: Artificial Sequence
<220> FEATURE:
<223> OTHER INFORMATION: Nucleotide Primer

<400> SEQUENCE: 7
gcgagcccca ttttgctaga ctagaggatc tggg                                 34

<210> SEQ ID NO 8
<211> LENGTH: 34
<212> TYPE: DNA
<213> ORGANISM: Artificial Sequence
<220> FEATURE:
<223> OTHER INFORMATION: Nucleotide Primer

<400> SEQUENCE: 8
cccagatcct ctagtctagc aaaatggggc tcgc                                 34

<210> SEQ ID NO 9
<211> LENGTH: 40
<212> TYPE: DNA
<213> ORGANISM: Artificial Sequence
<220> FEATURE:
<223> OTHER INFORMATION: Nucleotide Primer

<400> SEQUENCE: 9
cctgcgagcc ccatttccct gttagactag aggatctggg                           40

<210> SEQ ID NO 10
<211> LENGTH: 40
<212> TYPE: DNA
<213> ORGANISM: Artificial Sequence
<220> FEATURE:
<223> OTHER INFORMATION: Nucleotide Primer

<400> SEQUENCE: 10
cccagatcct ctagtctaac agggaaatgg ggctcgcagg                           40

<210> SEQ ID NO 11
<211> LENGTH: 30
<212> TYPE: DNA
<213> ORGANISM: Artificial Sequence
<220> FEATURE:
<223> OTHER INFORMATION: Nucleotide Primer

<400> SEQUENCE: 11
gccctggagc tccaggtcct caacgtgccc                                      30

<210> SEQ ID NO 12
<211> LENGTH: 30
<212> TYPE: DNA
<213> ORGANISM: Artificial Sequence
<220> FEATURE:
<223> OTHER INFORMATION: Nucleotide Primer

<400> SEQUENCE: 12
gggcacgttg aggacctgga gctccagggc                                      30

<210> SEQ ID NO 13
<211> LENGTH: 25
<212> TYPE: DNA

```
<213> ORGANISM: Artificial Sequence
<220> FEATURE:
<223> OTHER INFORMATION: Nucleotide Primer

<400> SEQUENCE: 13
cgtgccccgg gtgatgaccc aggac                                    25

<210> SEQ ID NO 14
<211> LENGTH: 25
<212> TYPE: DNA
<213> ORGANISM: Artificial Sequence
<220> FEATURE:
<223> OTHER INFORMATION: Nucleotide Primer

<400> SEQUENCE: 14
gtcctgggtc atcacccggg gcacg                                    25

<210> SEQ ID NO 15
<211> LENGTH: 36
<212> TYPE: DNA
<213> ORGANISM: Artificial Sequence
<220> FEATURE:
<223> OTHER INFORMATION: Nucleotide Primer

<400> SEQUENCE: 15
tctagatacc cagtcttgcc tgcagcagtc acggaa                        36

<210> SEQ ID NO 16
<211> LENGTH: 36
<212> TYPE: DNA
<213> ORGANISM: Artificial Sequence
<220> FEATURE:
<223> OTHER INFORMATION: Nucleotide Primer

<400> SEQUENCE: 16
ttccgtgact gctgcaggca agactgggta tctaga                        36

<210> SEQ ID NO 17
<211> LENGTH: 28
<212> TYPE: DNA
<213> ORGANISM: Artificial Sequence
<220> FEATURE:
<223> OTHER INFORMATION: Nucleotide Primer

<400> SEQUENCE: 17
cggatggcag cgcggactcc tgcaaggg                                 28

<210> SEQ ID NO 18
<211> LENGTH: 28
<212> TYPE: DNA
<213> ORGANISM: Artificial Sequence
<220> FEATURE:
<223> OTHER INFORMATION: Nucleotide Primer

<400> SEQUENCE: 18
cccttgcagg agtccgcgct gccatccg                                 28

<210> SEQ ID NO 19
<211> LENGTH: 26
<212> TYPE: DNA
<213> ORGANISM: Artificial Sequence
<220> FEATURE:
<223> OTHER INFORMATION: Nucleotide Primer

<400> SEQUENCE: 19
ccgtgggcca ccctggggtg tacacc                                   26
```

```
<210> SEQ ID NO 20
<211> LENGTH: 26
<212> TYPE: DNA
<213> ORGANISM: Artificial Sequence
<220> FEATURE:
<223> OTHER INFORMATION: Nucleotide Primer

<400> SEQUENCE: 20
ggtgtacacc ccagggtggc ccacgg                                          26
```